(12) United States Patent
Yaguchi

(10) Patent No.: US 10,561,300 B2
(45) Date of Patent: Feb. 18, 2020

(54) IMAGE PROCESSING APPARATUS, IMAGE PROCESSING METHOD, AND IMAGE PROCESSING PROGRAM

(71) Applicant: OLYMPUS CORPORATION, Tokyo (JP)

(72) Inventor: Yoichi Yaguchi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/208,651

(22) Filed: Dec. 4, 2018

(65) Prior Publication Data

US 2019/0099060 A1    Apr. 4, 2019

Related U.S. Application Data

(63) Continuation of application No. PCT/JP2016/067447, filed on Jun. 10, 2016.

(51) Int. Cl.
*G06T 7/12* (2017.01)
*A61B 1/00* (2006.01)
(Continued)

(52) U.S. Cl.
CPC ...... *A61B 1/00039* (2013.01); *A61B 1/00009* (2013.01); *A61B 1/317* (2013.01); *G06T 7/0012* (2013.01); *A61B 1/041* (2013.01)

(58) Field of Classification Search
None
See application file for complete search history.

(56) References Cited

U.S. PATENT DOCUMENTS

| 2005/0215854 A1* | 9/2005 | Ozaki | A61B 1/00009 600/109 |
| 2015/0264264 A1* | 9/2015 | Shiraki | H04N 5/23267 348/68 |

FOREIGN PATENT DOCUMENTS

| JP | 2005-278888 A | 10/2005 |
| JP | 2006-061274 A | 3/2006 |

(Continued)

OTHER PUBLICATIONS

Brejl, "Object Localization and Border Detection Criteria Design in Edge-Based Image Segmentation: Automated Learning from Examples" (Year: 2000).*

(Continued)

*Primary Examiner* — Eileen M Adams
(74) *Attorney, Agent, or Firm* — Scully, Scott, Murphy & Presser, P.C.

(57) ABSTRACT

An image processing apparatus includes a processor to: sequentially acquire plural subject images; select a detection target image from the plural subject images; detect the location of interest in the detection target image; generate spatial information of a superimposed object indicating the location of interest on one of the plural subject images; select a superimposition target image to be superimposed, from the plural subject images; generate inter-image correspondence information between the detection target image and the superimposition target image; correct the spatial information of the superimposed object, based on the inter-image correspondence information; and superimpose the superimposed object on the superimposition target image. The processor is configured to repeatedly execute the selecting the superimposition target image, the generating the inter-image correspondence information, the correcting the spatial information, and the superimposing the superim- (Continued)

posed object, until the spatial information of the superimposed object is generated for the detection target image.

16 Claims, 14 Drawing Sheets

(51) Int. Cl.
*A61B 1/317* (2006.01)
*G06T 7/00* (2017.01)
*A61B 1/04* (2006.01)

(56) References Cited

FOREIGN PATENT DOCUMENTS

| JP | 2010-172673 A | 8/2010 |
|---|---|---|
| JP | 2014-220618 A | 11/2014 |
| JP | 2015-171450 A | 10/2015 |

OTHER PUBLICATIONS

International Search Report dated Aug. 23, 2016 issued in PCT/JP2016/067447.

\* cited by examiner

IMAGE PROCESSING APPARATUS, IMAGE PROCESSING METHOD, AND IMAGE PROCESSING PROGRAM

CROSS-REFERENCE TO RELATED APPLICATION

This application is a continuation of International Application No. PCT/JP2016/067447, filed on Jun. 10, 2016, the entire contents of which are incorporated herein by reference.

BACKGROUND

The present disclosure relates to an image processing apparatus, an image processing method, and a non-transitory computer-readable storage medium storing an image processing program.

In the past, endoscope devices have been widely used for various examinations in the medical field and the industrial field. Among these endoscope devices, medical endoscope devices enable acquisition of in-vivo images (subject images) of subjects, such as patients, without incision of the subjects, by inserting elongated and flexible insertion units each having an imaging element, which has plural pixels and is provided at a distal end thereof, into the subjects, and thus the medical endoscope devices place smaller burdens on the subjects and have come into wide use.

In such an endoscope device, as a result of image analysis, information (hereinafter, also referred to as an object) specifying a location of interest, such as a result of lesion detection, is displayed on an observation screen, with the information being superimposed on a subject image. Known as a technique for superimposing an object on a subject image is a technique of: performing processing of detecting and cutting out, as an object, a moving object (a location of interest) in a captured image; and superimposing the object on the acquired captured image at the time of completion of this processing (for example, see Japanese Laid-open Patent Publication No. 2014-220618).

SUMMARY

The present disclosure is directed to an image processing apparatus, an image processing method, and an image processing program.

According to a first aspect of the present disclosure, an image processing apparatus is provided which includes a processor comprising hardware, the processor being configured to: sequentially acquire plural subject images; select a detection target image from the plural subject images; detect a location of interest in the detection target image; generate spatial information of a superimposed object, the superimposed object being to be superimposed on any one of the plural subject images and to indicate the location of interest; select a superimposition target image from the plural subject images, the superimposition target image being a target on which the superimposed object is to be superimposed; generate inter-image correspondence information between the detection target image and the superimposition target image; correct the spatial information of the superimposed object, based on the inter-image correspondence information; and superimpose the superimposed object on the superimposition target image, the superimposed object having the corrected spatial information, wherein the processor is further configured to repeatedly execute the selecting the superimposition target image, the generating the inter-image correspondence information, the correcting the spatial information, and the superimposing the superimposed object, until the spatial information of the superimposed object is generated for the detection target image.

According to a second aspect of the present disclosure, an image processing method is provided which includes sequentially acquiring plural subject images; selecting a detection target image from the plural subject images; detecting a location of interest in the detection target image; generating spatial information of a superimposed object, the superimposed object being to be superimposed on any of the plural subject images and to indicate the location of interest; selecting a superimposition target image from the plural subject images, the superimposition target image being a target on which the superimposed object is to be superimposed; generating inter-image correspondence information between the detection target image and the superimposition target image; correcting the spatial information of the superimposed object, based on the inter-image correspondence information; and superimposing the superimposed object on the superimposition target image, the superimposition target image having the corrected spatial information, wherein the selecting the superimposition target image, the generating the inter-image correspondence information, the correcting the spatial information, and the superimposing the superimposed object are repeatedly executed, until the spatial information of the superimposed object is generated for the detection target image.

According to a third aspect of the present disclosure, a non-transitory computer-readable storage medium is provided which stores an image processing program that causes a computer to execute a process. The process includes sequentially acquiring plural subject images; selecting a detection target image from the plural subject images; detecting a location of interest in the detection target image; generating spatial information of a superimposed object, the superimposed object being to be superimposed on any of the plural subject images and to indicate the location of interest; selecting a superimposition target image from the plural subject images, the plural subject images being a target on which the superimposed object is to be superimposed; generating inter-image correspondence information between the detection target image and the superimposition target image; correcting the spatial information of the superimposed object, based on the inter-image correspondence information; and superimposing the superimposed object on the superimposition target image, the superimposed object having the corrected spatial information, wherein the selecting the superimposition target image, the generating the inter-image correspondence information, the correcting the spatial information, and the superimposing the superimposed object are repeatedly executed, until the spatial information of the superimposed object is generated for the detection target image.

The above and other features, advantages and technical and industrial significance of this disclosure will be better understood by reading the following detailed description of presently preferred embodiments of the disclosure, when considered in connection with the accompanying drawings.

DETAILED DESCRIPTION OF THE PREFERRED EMBODIMENTS

Hereinafter, modes for carrying out the present disclosure will be described in detail, together with the drawings. The present disclosure is not limited by the following embodiments. Further, the drawings referred to in the following description schematically depict shapes, sizes, and positional relations merely to an extent that allows substance of the present disclosure to be understood.

That is, the present disclosure is not limited only to the shapes, sizes, and positional relations exemplified by the drawings. Further, in the description, any components that are the same will be assigned with the same reference sign.

First Embodiment

Figure 1:
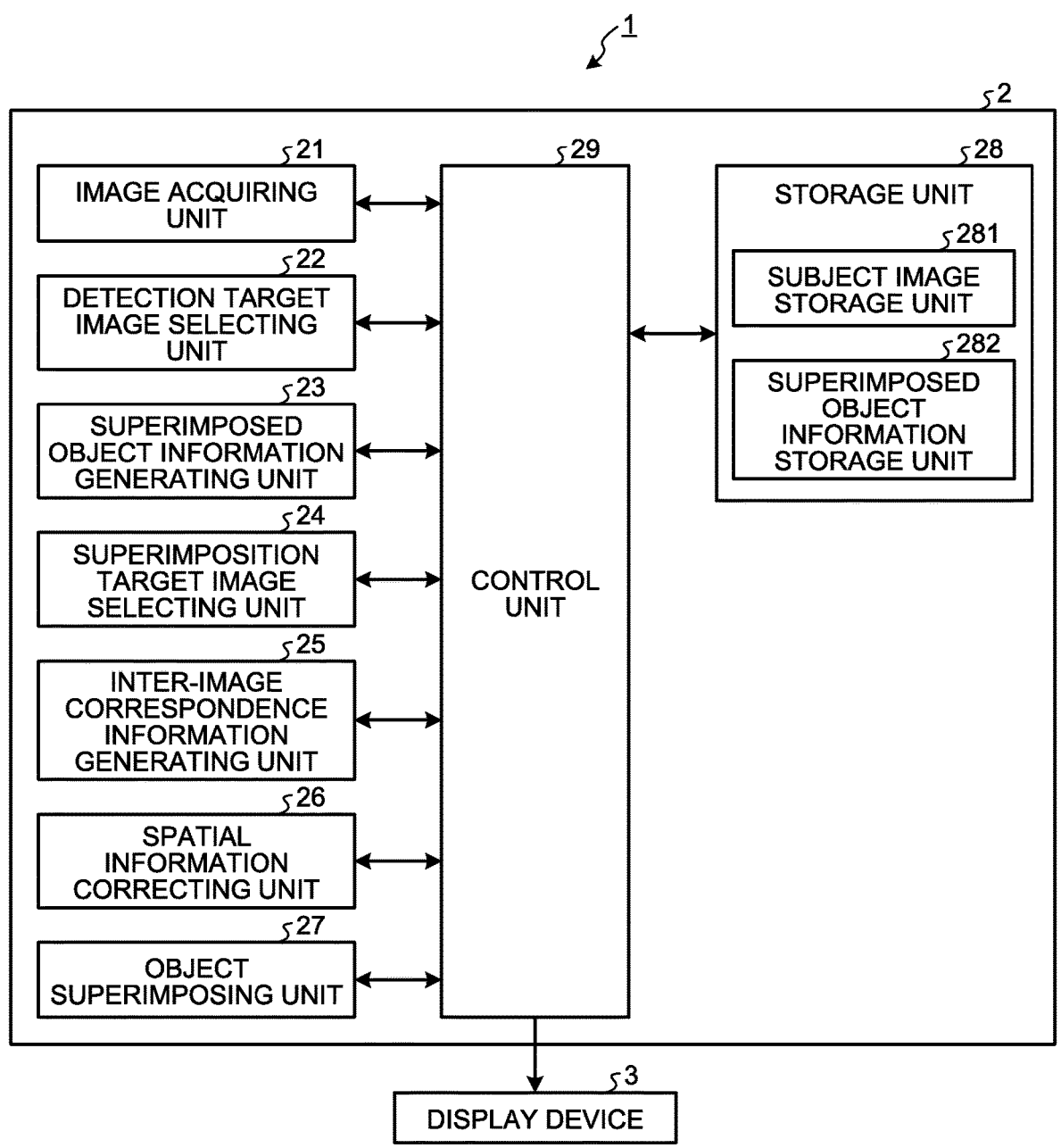
FIG. 1 is a block diagram depicting a functional configuration of an image processing system according to a first embodiment of the present disclosure.

FIG. 1 is a block diagram depicting a functional configuration of an image processing system 1 according to a first embodiment of the present disclosure. The image processing system 1 depicted in FIG. 1 includes an image processing apparatus 2, and a display device 3. By processing an image that has been acquired, the image processing apparatus 2 generates an image signal for display, which is displayed by the display device 3. The display device 3 receives the image signal generated by the image processing apparatus 2 via a video cable, and displays thereon an image corresponding to the image signal. The display device 3 is configured by use of liquid crystal or organic electroluminescence.

The image processing apparatus 2 includes an image acquiring unit 21, a detection target image selecting unit 22, a superimposed object information generating unit 23, a superimposition target image selecting unit 24, an inter-image correspondence information generating unit 25, a spatial information correcting unit 26, an object superimposing unit 27, a storage unit 28, and a control unit 29.

The image acquiring unit 21 sequentially receives, from outside, image signals including subject images, in temporal sequence; or acquires, in temporal sequence, images that have been stored in the storage unit 28. The image acquiring unit 21 generates an image signal including, for example, a three-chip subject image imparted with R, G, and B color components, by performing signal processing, such as noise removal, A/D conversion, or synchronization processing (which is performed when, for example, an imaging signal for each color component has been acquired by use of a color filter or the like) as necessary. The image acquiring unit 21 inputs the acquired image signals or the image signal that has been signal-processed, to the superimposed object information generating unit 23 and the storage unit 28. The image acquiring unit 21 may perform OB clamping processing, gain adjustment processing, or the like, other than the above mentioned synchronization processing or the like. Examples of the images include: images including a subject, such as a human; and subject images, such as images of a body cavity in a subject, the subject images having been acquired (captured) in temporal sequence by an endoscope (which may be a capsule-type endoscope) and including a subject.

The detection target image selecting unit 22 selects, from the subject images, a detection target subject image (hereinafter, also referred to as a detection target image), from which a location to be noted (hereinafter, also referred to as a location of interest) in the subject images is to be detected.

The superimposed object information generating unit 23 generates spatial information of a superimposed object to be superimposed and placed on a location of interest in a subject image based on an image signal input from the image acquiring unit 21. A location of interest is, for example, a lesion location in an in-vivo image of a subject. A superimposed object is an object that is superimposed on a location of interest in a subject image and that specifies the location of interest. More specifically, for example, if a subject image is an image of a body cavity in a subject, a superimposed object is a rectangular frame surrounding a lesion site. A superimposition target subject image (hereinafter, also referred to as a superimposition target image), on which a superimposed object is to be superimposed, is a subject image different from a detection target image, and a subject image that is temporally later than the detection target image. Further, spatial information is coordinate information of a space where a frame of a superimposed object is positioned when a subject image is viewed on a two-dimensional plane, and is information related to coordinates representing this space, for example, coordinates of four corners of a rectangular frame.

Incidentally, the spatial information may be: any of information representing an area mask having a transparent window that is transparent over a location of interest, and information representing a contour line surrounding a location of interest; or may be information that is a combination of coordinate information, an area mask, and a contour line.

The superimposed object information generating unit 23 may generate the spatial information of a superimposed object by using, for example, the technique described in "Object Detection with Discriminatively Trained Part-Based Models" by Pedro F. Felzenszwalb, Ross B. Girshick, David McAllester, and Deva Ramanan, PAMI 2010.

The superimposition target image selecting unit 24 selects, from the subject images, a superimposition target image, on which the superimposed object is to be superimposed and which is to be displayed on the display device 3, the superimposed object having the spatial information generated by the superimposed object information generating unit 23.

The inter-image correspondence information generating unit 25 generates inter-image correspondence information that is information indicating estimated correspondence between: the detection target image, which is the subject image that has been selected by the detection target image selecting unit 22, and from which the spatial information of the superimposed object has been generated by the superimposed object information generating unit 23; and the superimposition target image that has been selected by the superimposition target image selecting unit 24. Specifically, the inter-image correspondence information generating unit 25 generates inter-image correspondence information between the detection target image and the superimposition target image, the inter-image correspondence information being expressed by at least one type of coordinate transformation selected from: non-rigid transformation; homography transformation; affine transformation; linear transformation; scale transformation; rotational transformation; and translation. In the generation of the inter-image correspondence information, for example, the technique described in Japanese Patent Application Laid-open No. 2007-257287 may be used.

The spatial information correcting unit 26 corrects the spatial information of the superimposed object generated by the superimposed object information generating unit 23, according to the inter-image correspondence information generated by the inter-image correspondence information generating unit 25. In this first embodiment, the spatial information correcting unit 26 corrects, based on coordinate transformation parameters that are the inter-image correspondence information generated by the inter-image correspondence information generating unit 25, coordinate information that is the spatial information of the superimposed object generated by the superimposed object information generating unit 23.

Based on the spatial information of the superimposed object generated by the superimposed object information generating unit 23, the object superimposing unit 27 superimposes the superimposed object on the superimposition target image.

Figure 2:
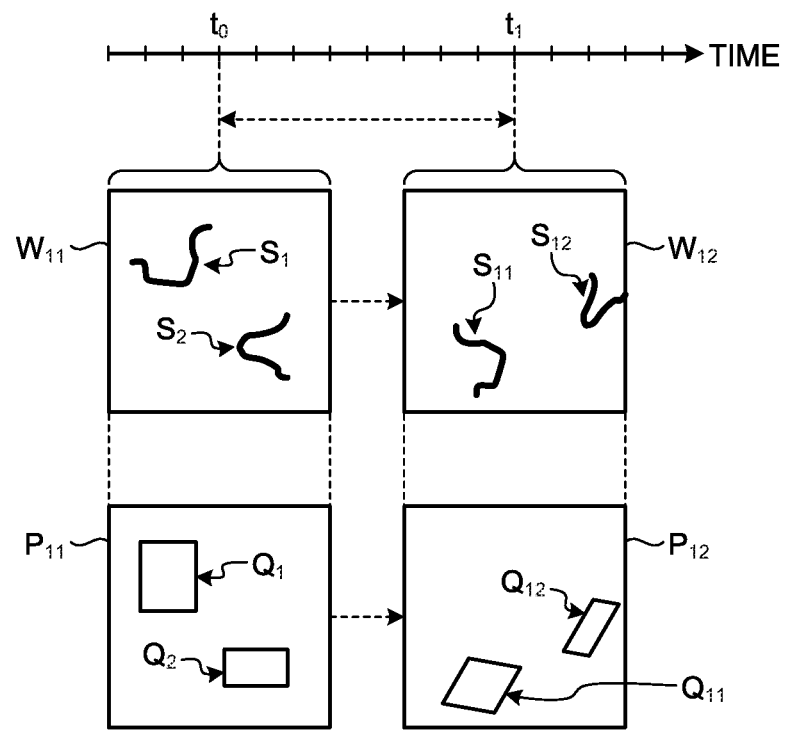
FIG. 2 is a diagram for explanation of object superimposition processing performed by an image processing apparatus according to the first embodiment of the present disclosure.
Figure 3:
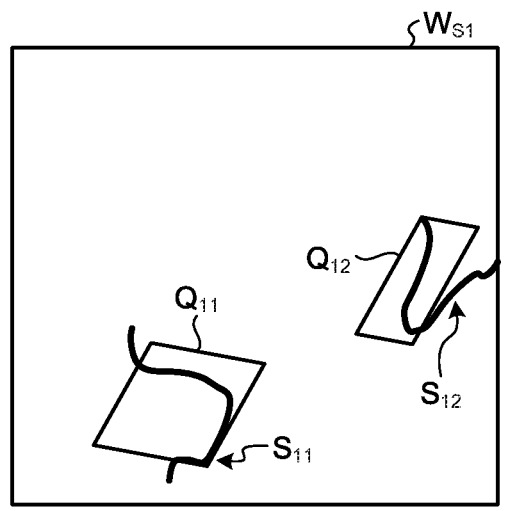
FIG. 3 is a diagram depicting an object superimposition image generated by the image processing apparatus according to the first embodiment of the present disclosure.

FIG. 2 is a diagram for explanation of object superimposition processing performed by the image processing apparatus 2 according to the first embodiment of the present disclosure. FIG. 3 is a diagram depicting an object superimposition image generated by the image processing apparatus according to the first embodiment of the present disclosure. The time axis depicted in FIG. 2 is provided with scale marks according to intervals, at which the image acquiring unit 21 acquires the subject images frame by frame. If, for example, a subject image $W_{11}$ at a time $t_0$ has been selected as the detection target image by the detection target image selecting unit 22, the superimposed object information generating unit 23 detects a location of interest from the subject image $W_{11}$, and generates, from the subject image $W_{11}$, spatial information of a superimposed object specifying this location of interest. The superimposed object information generating unit 23 generates, as spatial information, for example, as depicted in FIG. 2, coordinates of four corners of each of superimposed objects $Q_1$ and $Q_2$ in an object space $P_{11}$ corresponding to an outer edge of the subject image $W_{11}$. The superimposed objects $Q_1$ and $Q_2$ are rectangular frames surrounding lesion sites $S_1$ and $S_2$.

If the superimposed object information generating unit 23 completes the generation of the spatial information at a time $t_1$, the superimposition target image selecting unit 24 selects, as the superimposition target image to be displayed on the display device 3, for example, a subject image $W_{12}$ (see FIG. 2) corresponding to this time $t_1$. The subject image $W_{12}$ has lesion sites $S_{11}$ and $S_{12}$ displayed thereon, the lesion sites $S_{11}$ and $S_{12}$ having changed from those of the lesion sites $S_1$ and $S_2$ in the subject image $W_{11}$ in terms of their positions and orientations. Incidentally, the image acquiring unit 21 acquires plural subject images other than the subject images $W_{11}$ and $W_{12}$, in a time period from the time $t_0$ to the time $t_1$. Namely, it takes a certain time period, which is long enough to acquire subject images of a few frames, from the start of the generation of the spatial information by the superimposed object information generating unit 23 until the completion of the generation. In FIG. 2, for explanation, only the subject images $W_{11}$ and $W_{12}$ are depicted.

The inter-image correspondence information generating unit 25 generates inter-image correspondence information including transformation parameters representing correspondence between: the subject image $W_{11}$ that has been selected by the detection target image selecting unit 22 and that is the detection target image, from which the spatial information of the superimposed objects $Q_1$ and $Q_2$ has been generated by the superimposed object information generating unit 23; and the subject image $W_{12}$ that is the superimposition target image selected by the superimposition target image selecting unit 24. The inter-image correspondence information generating unit 25 generates the inter-image correspondence information by using, for example, all of pixels of these subject images.

The inter-image correspondence information generating unit 25 generates, for the subject image $W_{11}$ and the subject image $W_{12}$, inter-image correspondence information expressed by at least one type of coordinate transformation selected from: non-rigid transformation; homography transformation; affine transformation; linear transformation; scale transformation; rotational transformation; and translation.

The spatial information correcting unit 26 generates, as corrected spatial information of the superimposed objects (for example, superimposed objects $Q_{11}$ and $Q_{12}$), spatial information resulting from transformation of the coordinates of the spatial information of the superimposed objects, based on the transformation parameters of the inter-image correspondence information. Thereby, the spatial information of the superimposed objects $Q_{11}$ and $Q_{12}$ in an object space $P_{12}$ corresponding to an outer edge of the subject image $W_{12}$ is generated. Specifically, the spatial information correcting unit 26 generates the corrected spatial information of the superimposed objects by transforming the coordinates of the spatial information of the superimposed objects generated by the superimposed object information generating unit 23, based on the coordinate transformation parameters that are the inter-image correspondence information.

By generating the superimposed objects $Q_{11}$ and $Q_{12}$ (see FIG. 2) based on the spatial information corrected by the spatial information correcting unit 26 and superimposing these superimposed objects $Q_{11}$ and $Q_{12}$ on the subject image $W_{12}$ (see FIG. 2), for example, the object superimposing unit 27 generates, as depicted in FIG. 3, a superimposed image $W_{s1}$ having parts of the lesion sites $S_{11}$ and $S_{12}$ surrounded by the superimposed objects $Q_{11}$ and $Q_{12}$.

Figure 4:
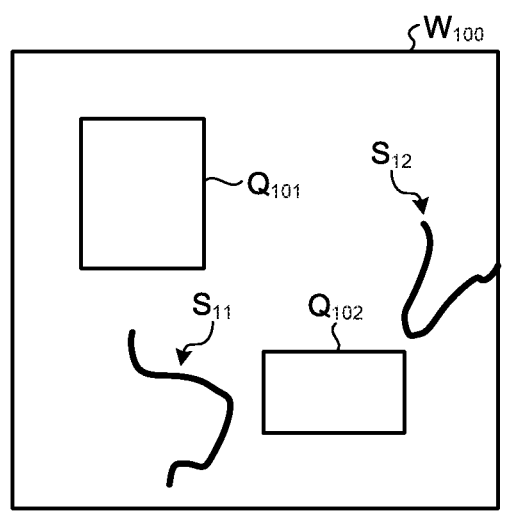
FIG. 4 is a diagram depicting an object superimposition image generated by conventional processing.

FIG. 4 is a diagram depicting an object superimposition image of a comparative example, generated without the correction of the spatial information of the superimposed object. As illustrated in FIG. 4, superimposed objects $Q_{101}$ and $Q_{102}$ are not properly placed in relation to the lesion sites $S_{11}$ and $S_{12}$ in a superimposed image $W_{100}$, when the spatial information of the superimposed objects is not corrected.

In contrast, according to this first embodiment, even when the superimposed objects $Q_1$ and $Q_2$ are extracted from the subject image $W_{11}$ acquired at the time t0 and superimposed on the subject image $W_{12}$ acquired at the time t1, where the lesion sites $S_{11}$ and $S_{12}$ have been changed from the lesion sites $S_1$ and $S_2$ in the subject image $W_{11}$ in terms of positions and orientations, the superimposed objects $Q_{11}$ and $Q_{12}$ may be placed at appropriate positions in relation to the lesion sites $S_{11}$ and $S_{12}$, because the spatial information of the superimposed objects $Q_{11}$ and $Q_{12}$ are obtained by correcting the spatial information of the superimposed objects $Q_1$ and $Q_2$.

Referring back to FIG. 1, the storage unit 28 stores therein: various programs for operation of the image processing system 1 including the image processing apparatus 2, for example, an image processing program; and data including various parameters needed for the operation of the image processing system 1. The storage unit 28 is realized by use of a semiconductor memory, such as a flash memory or a dynamic random access memory (DRAM).

The storage unit 28 has a subject image storage unit 281 that stores the subject images acquired by the image acquiring unit 21, and a superimposed object information storage unit 282 that stores the spatial information of the superimposed objects generated by the superimposed object information generating unit 23. The superimposed object information storage unit 282 stores only the latest spatial information of the superimposed objects, and if newly generated spatial information of the superimposed objects is input, the superimposed object information storage unit 282 updates the latest spatial information of the superimposed objects to the input spatial information of the superimposed objects.

The control unit 29 is configured by use of a central processing unit (CPU) or the like, controls the units forming the image processing apparatus 2, and controls input and output of information to and from these units.

Figure 5:
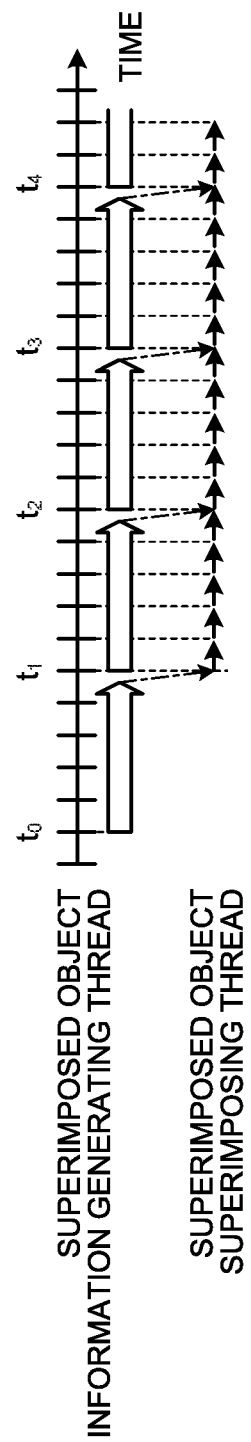
FIG. 5 is a diagram for explanation of an outline of superimposition processing for a superimposed object, the superimposition processing being performed by the image processing apparatus according to the first embodiment of the present disclosure.

Next, superimposition processing for a superimposed object performed by the units of the image processing apparatus 2 will be described by reference to the drawings. FIG. 5 is a diagram for explanation of an outline of superimposition processing for a superimposed object performed by the image processing apparatus according to the first embodiment of the present disclosure. FIG. 5 is given scale marks corresponding to time intervals, at which the subject images are input frame by frame. According to FIG. 5, the superimposed object information generating unit 23 requires a time period enough to subject images of five frames when generating spatial information of a superimposed object from a subject image. While the superimposed object information generating unit 23 is generating the spatial information of the corrected superimposed object through a superimposed object information generating thread, the object superimposing unit 27 performs superimposition processing by using spatial information of the superimposed object that was generated last time, through a superimposed object superimposing thread. In this superimposition processing, the inter-image correspondence information generating unit 25 generates inter-image correspondence information for: a detection target image, from which the spatial information of the superimposed object was generated last time; and a superimposition target image selected by the superimposition target image selecting unit 24. As described above, in the superimposition processing for the superimposed object, until the spatial information of the superimposed object is updated, the latest spatial information of the superimposed object stored in the superimposed object information storage unit 282 is repeatedly used.

Figure 6:
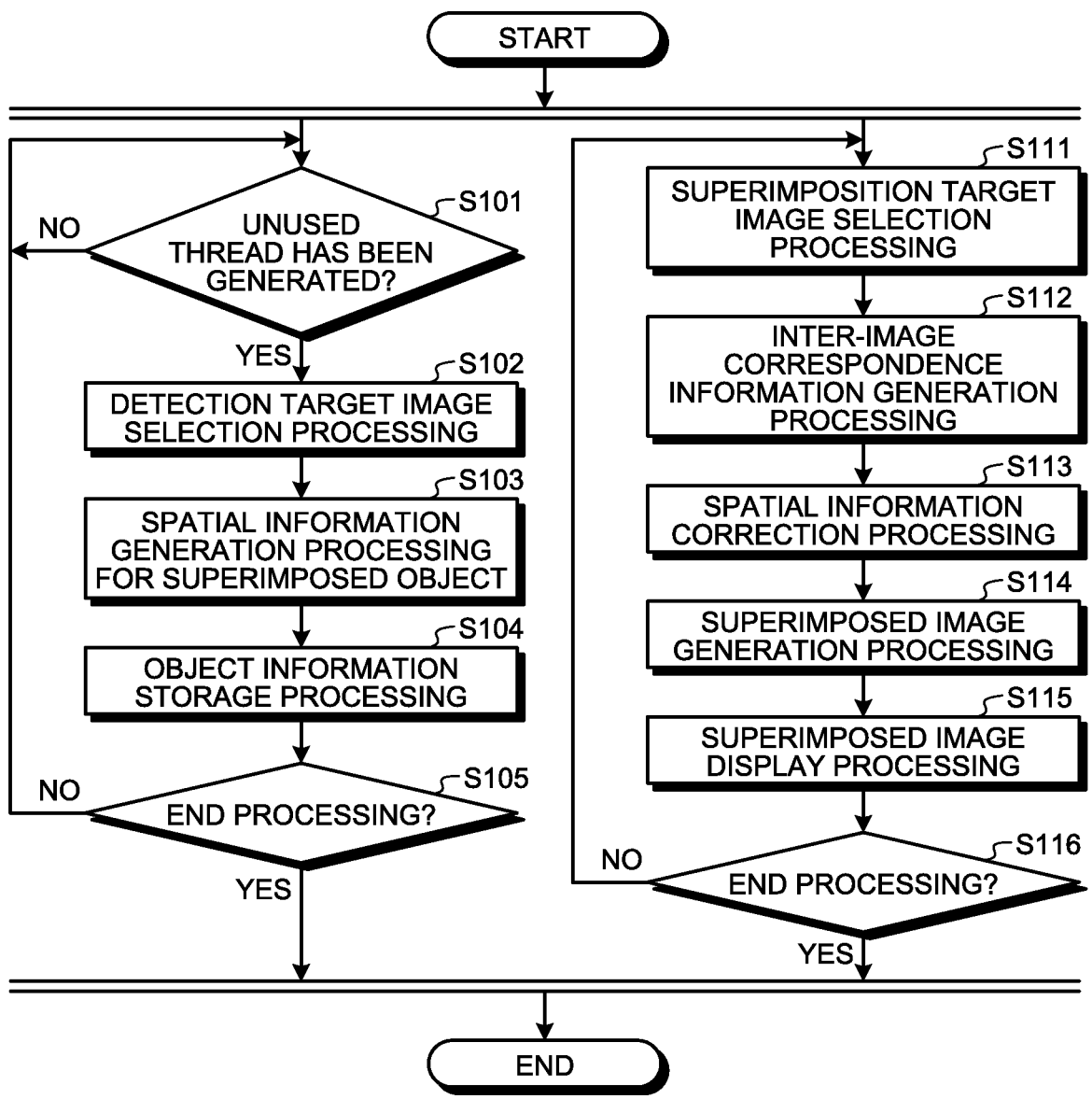
FIG. 6 is a flow chart depicting an outline of the superimposition processing for a superimposed object performed by the image processing apparatus according to the first embodiment of the present disclosure.

FIG. 6 is a flow chart depicting an outline of superimposition processing for a superimposed object performed by the image processing apparatus 2 according to the first embodiment of the present disclosure. Hereinafter, description will be made on the assumption that each unit operates under control by the control unit 29. The image processing apparatus 2 performs processing of generating spatial information of a superimposed object (Steps S101 to S105) and processing of superimposing a superimposed object on a superimposition target image (Steps S111 to S116), in parallel.

First, the control unit 29 determines whether or not an unused thread has been generated in the CPU (Step S101). For example, by referring to a usage rate of the CPU or the like, the control unit 29 determines whether or not an unused thread usable in generation of spatial information of a superimposed object has been generated. If the control unit 29 determines that an unused thread has not been generated (Step S101: No), the control unit 29 repeats checking whether or not an unused thread has been generated. On the contrary, if the control unit 29 determines that an unused thread has been generated (Step S101: Yes), the processing is advanced to Step S102.

At Step S102, the detection target image selecting unit 22 selects a detection target image, from which a location of interest is to be detected. The detection target image selecting unit 22 selects a subject image serving as the detection target image, from the subject images that have been acquired by the image acquiring unit 21 and stored in the subject image storage unit 281.

At Step S103, the superimposed object information generating unit 23 generates, from the detection target image (for example, the above described subject image $W_{11}$: see FIG. 2), spatial information of a superimposed object to be superimposed on a subject image input from the image acquiring unit 21.

At Step S104 subsequent to Step S103, the superimposed object information storage unit 282 stores the spatial information generated by the superimposed object information generating unit 23. The control unit 29 advances the processing to Step S105 after the superimposed object information storage unit 282 stores the spatial information of the superimposed object.

At Step S105, the control unit 29 determines whether or not an instruction to end the generation processing and the storage processing for spatial information of a superimposed object has been input. If the control unit 29 determines that the instruction to end these flows of processing has not been input (Step S105: No), the control unit 29 advances the processing to Step S101 and repeats the above described generation processing and storage processing for spatial information of a superimposed object. On the contrary, if the control unit 29 determines that the instruction to end the generation processing and the storage processing for spatial information of a superimposed object has been input (Step S105: Yes), the control unit 29 ends the generation processing and the storage processing for the spatial information of the superimposed object.

In parallel with the above described generation processing for spatial information of a superimposed object, the control unit 29 performs superimposition processing for a superimposed object (Steps S111 to S116). First, the superimposition target image selecting unit 24 selects a superimposition target image (for example, the above described subject image $W_{12}$) to be displayed on the display device 3 with a superimposed object being superimposed thereon (Step S111). The superimposition target image selecting unit 24 refers to the subject image storage unit 281, and selects, as the superimposition target image, a first subject image to be acquired right after completion of the generation of the spatial information of the superimposed object.

At Step S112 subsequent to Step S111, the inter-image correspondence information generating unit 25 generates inter-image correspondence information for: the detection target image that has been used by the superimposed object information generating unit 23; and the superimposition target image, which has been selected by the superimposition target image selecting unit 24, and on which the superimposed object is to be superimposed. Specifically, at Step S112, the inter-image correspondence information generating unit 25 acquires the detection target image corresponding to the spatial information of the superimposed object stored in the superimposed object information storage unit 282, and generates inter-image correspondence information representing correspondence between: the acquired detection target image; and the superimposition target image selected by the superimposition target image selecting unit 24.

At Step S113 subsequent to Step S112, the spatial information correcting unit 26 corrects the spatial information by transforming, based on transformation parameters of the inter-image correspondence information generated by the inter-image correspondence information generating unit 25, coordinates of the spatial information.

At Step S114 subsequent to Step S113, the object superimposing unit 27 generates a superimposed object having the spatial information corrected by the spatial information correcting unit 26, and generates a superimposed image by superimposing this superimposed object on the superimposition target image. The object superimposing unit 27 generates, for example, as depicted in FIG. 3, the superimposed image $W_{s1}$ having parts of the lesion sites $S_{11}$ and $S_{12}$ surrounded by the superimposed objects $Q_{11}$ and $Q_{12}$.

At Step S115 subsequent to Step S114, under control by the control unit 29, control for display of the superimposed image (for example, the superimposed image $W_{s1}$) generated by the object superimposing unit 27, on the display device 3, is performed. After displaying the superimposed image on the display device 3, the control unit 29 advances the processing to Step S116.

At Step S116, the control unit 29 determines whether or not an instruction to end the superimposition processing for a superimposed object has been input. If the control unit 29 determines that the instruction to end the superimposition processing for a superimposed object has not been input (Step S116: No), the control unit 29 advances the processing to Step S111, and repeats the above described superimposition processing for a superimposed object. On the contrary, if the control unit 29 determines that the instruction to end the superimposition processing for a superimposed object has been input (Step S116: Yes), the control unit 29 ends the superimposition processing on the superimposed object.

A time period, in which subject images of a few frames are input, is required from start to completion of the generation of spatial information of a superimposed object for one detection target image by the superimposed object information generating unit 23. In contrast, the superimposed object superimposition processing (the above described Step S111 to Step S115) where a superimposition target image is displayed on the display device 3 with a superimposed object superimposed thereon requires a time period equal to or less than a time interval, in which a subject image of one frame is input. Therefore, in the object superimposition processing according to the first embodiment, subject images sequentially input to the image processing apparatus 2 are selected as superimposition target images, and superimposed objects are superimposed on the superimposition target images by use of spatial information of a superimposed object stored in the superimposed object information storage unit 282.

According to the above described first embodiment, while the superimposed object information generating unit 23 is generating spatial information of a superimposed object for one detection target image, the object superimposing unit 27 performs correction based on the latest spatial information of a superimposed object stored in the superimposed object information storage unit 282 by repeatedly using the latest spatial information, and superimposes the superimposed object on a superimposition target image. Thereby, even in a case where a superimposed object detected from a detection target image for the superimposed object is superimposed on a superimposition target image temporally different from the detection target image, positional displacement of the superimposed object in relation to a position of a location of interest in the superimposition target image is able to be reduced, and thus subject images sequentially acquired by the image acquiring unit 21 are able to be displayed on the display device 3 with superimposed objects being superimposed thereon, the superimposed objects having been reduced in positional displacement.

In the above described first embodiment, the spatial information correcting unit 26 may further correct spatial information that has been corrected, by minutely changing coordinates, based on, for example, Mean Squared Error between pixel values of a superimposition area of the superimposed object corresponding to the spatial information that has been corrected in the superimposition target image, and pixel values of a superimposition area of the superimposed object corresponding to the non-corrected spatial information in the detection target image. When the spatial information correcting unit 26 corrects the spatial information further like this, the spatial information stored in the superimposed object information storage unit 282 is updated to the spatial information generated by this additional correction.

Further, in the above described first embodiment, image processing, such as processing for enhancement of a contour of the subject (edge enhancement processing), may be performed on a superimposed object, for which the spatial information has been corrected.

Further, according to the description of the first embodiment, inter-image correspondence information is generated by use of all of pixels of a subject image, but for reduction of the amount of calculation, the subject image may be downsized, and inter-image correspondence information may be generated by use of the downsized subject image.

Further, according to the description of the first embodiment, the superimposed object information storage unit 282 stores therein only the latest spatial information of a superimposed object, but the superimposed object information storage unit 282 may sequentially store therein generated spatial information in association with detection target images. In this case, the inter-image correspondence information generating unit 25 generates inter-image correspondence information between a detection target image corresponding to the latest spatial information of a superimposed object stored in the superimposed object information storage unit 282 and a superimposition target image. Further, the spatial information correcting unit 26 performs, based on inter-image correspondence information, correction of the latest spatial information of a superimposed object stored in the superimposed object information storage unit 282.

Further, according to the description of the first embodiment, superimposed objects are rectangular frames, but other than rectangular frames, the superimposed objects may be: oval or circular frames; shaped correspondingly to locations of interest; or objects with their inside filled in.

First Modified Example of First Embodiment

In this first modified example, the superimposed object information generating unit 23 performs generation processing for spatial information of a superimposed object by use of three threads in parallel.

Figure 7:
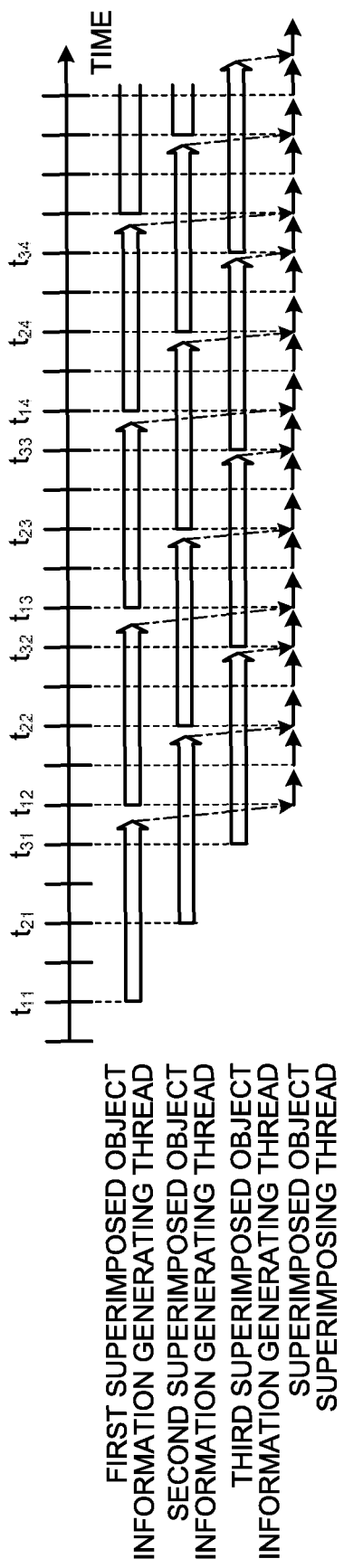
FIG. 7 is a diagram for explanation of an outline of superimposition processing for a superimposed object, the superimposition processing being performed by an image processing apparatus according to a first modified example of the first embodiment of the present disclosure.

FIG. 7 is a diagram for explanation of an outline of superimposition processing for a superimposed object performed by an image processing apparatus according to the first modified example of the first embodiment of the present disclosure. As depicted in FIG. 7, the superimposed object information generating unit 23 generates spatial information of a superimposed object by using a subject image acquired by the image acquiring unit 21, through parallel processing by use of three threads.

Specifically, the superimposed object information generating unit 23 generates spatial information of a superimposed object from subject images sequentially acquired by the image acquiring unit 21 by using a first superimposed object information generating thread, a second superimposed object information generating thread, and a third superimposed object information generating thread. The superimposed object information generating unit 23 starts generation processing for spatial information of a superimposed object for a subject image by using the first superimposed object information generating thread, at, for example, a time $t_{11}$.

Thereafter, at a time $t_{21}$ after elapse of a time period corresponding to two frames, by using the second superimposed object information generating thread, the superimposed object information generating unit 23 starts generation processing for spatial information of a superimposed object for another detection target image that is a subject image different from the detection target image that is being processed by the first superimposed object information generating thread. At a time $t_{31}$ after further elapse of a time period corresponding to two frames, the superimposed object information generating unit 23 starts generation processing for spatial information of a superimposed object for another subject image by using the third superimposed object information generating thread.

Further, at a time $t_{12}$ when the superimposed object spatial information generation processing started at the time $t_{11}$ is completed, the superimposed object information generating unit 23 starts generation processing for spatial information of a superimposed object for a new subject image by using the first superimposed object information generating thread. Thereafter, similarly, at times $t_{13}$ and $t_{14}$, the superimposed object information generating unit 23 starts generation processing for spatial information of superimposed objects for new subject images by using the first superimposed object information generating thread.

Further, as to the second superimposed object information generating thread, similarly, at a time $t_{22}$ when the superimposed object spatial information generation processing started at the time $t_{21}$ is completed, the superimposed object information generating unit 23 starts generation processing for spatial information of a superimposed object for a new subject image by using the second superimposed object information generating thread. Thereafter, at times $t_{23}$ and $t_{24}$, the superimposed object information generating unit 23 starts generation processing for spatial information of superimposed objects for new subject images by using the second superimposed object information generating thread.

As to the third superimposed object information generating thread, similarly, at a time $t_{32}$ when the superimposed object spatial information generation processing started at the time $t_{31}$ is completed, the superimposed object information generating unit 23 starts generation processing for spatial information of a superimposed object for a new subject image by using the third superimposed object information generating thread. Thereafter, at times $t_{33}$ and $t_{34}$, the superimposed object information generating unit 23 starts generation processing for spatial information of superimposed objects for new subject images by using the third superimposed object information generating thread.

The control unit 29 causes superimposition processing for superimposed objects to be sequentially executed through the superimposed object superimposing thread, from the time $t_{12}$ when the superimposed object spatial information generation processing started at the time $t_{11}$ is completed.

Thereby, the spatial information of the superimposed objects is updated more frequently than that in the above described first embodiment. Therefore, the object superimposing unit 27 may perform superimposition processing by using temporally close spatial information of a superimposed object.

According to this first modified example, superimposition processing may be performed by use of the spatial information of the superimposed object, the spatial information being obtained from temporally closer subject image than that in the above described first embodiment. Thereby, the superimposed object can be superimposed on the superimposition target image so that the superimposed object more accurately fits with the location of interest.

Further, according to the first modified example, the first superimposed object information generating thread, the second superimposed object information generating thread, and the third superimposed object information generating thread start the generation processing at different timings shifted with one another by two frames, timings of the generation of the spatial information of the superimposed objects started by the first superimposed object information generating thread, the second superimposed object information generating thread, and the third superimposed object information generating thread may be maintained evenly.

Incidentally, in the above-described first modified example, plural threads are provided for generation processing for spatial information of superimposed objects, but plural threads may be provided for object superimposition processing, or plural threads may be provided for each of generation processing for spatial information of superimposed objects, and object superimposition processing. For example, if there are four threads that are able to be used in processing: three threads may be provided for generation processing for spatial information of superimposed objects; three threads may be provided for superimposition processing for superimposed objects; or two threads may be provided for generation processing for spatial information of superimposed objects, and the remaining two threads may be provided for superimposition processing for the superimposed objects.

Second Modified Example of First Embodiment

Figure 8:
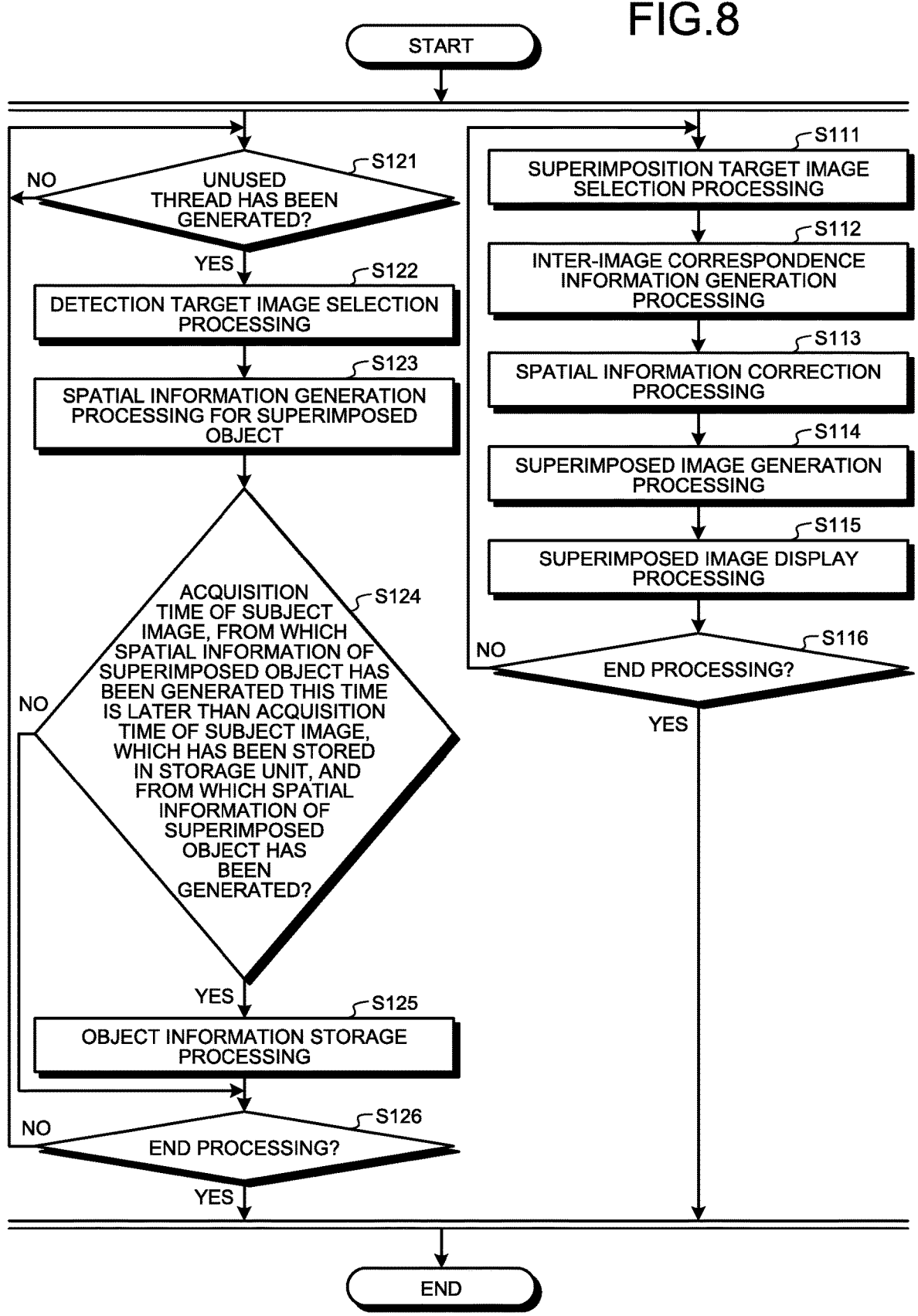
FIG. 8 is a flow chart depicting an outline of superimposition processing for a superimposed object, the superimposition processing being performed by an image processing apparatus according to a second modified example of the first embodiment of the present disclosure.

In this second modified example, when spatial information of superimposed objects is generated by use of plural threads, whether or not the spatial information of the superimposed objects is to be stored in the superimposed object information storage unit 282 is determined. FIG. 8 is a flow chart depicting an outline of superimposition processing for a superimposed object performed by an image processing apparatus according to the second modified example of the first embodiment of the present disclosure. Hereinafter, description will be made on the assumption that each unit operates under control by the control unit 29. In the processing performed by the image processing apparatus 2 according to this second modified example, processing for generation of spatial information of a superimposed object (Steps S121 to S126) and processing for superimposition of a superimposed object on a superimposition target image (Steps S111 to S116) are performed in parallel.

Firstly, the control unit 29 determines whether or not any unused thread has been generated (Step S121). If the control unit 29 determines that any unused thread has not been generated (Step S121: No), the control unit 29 repeats checking whether or not any unused thread has been generated. On the contrary, if the control unit 29 determines that an unused thread has been generated (Step S121: Yes), the processing is advanced to Step S122.

At Step S122, the detection target image selecting unit 22 selects a detection target image, from which a location of interest is to be detected. The detection target image selecting unit 22 selects a subject image serving as the detection target image, from the subject images, which have been acquired by the image acquiring unit 21 and stored in the subject image storage unit 281.

At Step S123, the superimposed object information generating unit 23 generates, from the detection target image, spatial information of any superimposed object to be superimposed on a subject image input from the image acquiring unit 21.

At Step S124 subsequent to Step S123, the control unit 29 compares a time of acquisition of the detection target image, from which the spatial information of the superimposed object has been generated by the superimposed object information generating unit 23 in Step S123 (hereinafter, referred to as a first acquisition time), with a time of acquisition of a detection target image corresponding to spatial information of a superimposed object stored in the superimposed object information storage unit 282 (hereinafter, referred to as a second acquisition time). A time of acquisition is a time, at which the image acquiring unit 21 acquired a detection target image. If the first acquisition time is earlier than the second acquisition time (Step S124: No), the control unit 29 advances the processing to Step S126. On the contrary, if the first acquisition time is later than the second acquisition time (Step S124: Yes), the control unit 29 advances the processing to Step S125.

At Step S125, the superimposed object information storage unit 282 stores the spatial information generated from the detection target image acquired at the first acquisition time by the superimposed object information generating unit 23. The control unit 29 advances the processing to Step S126 after the superimposed object information storage unit 282 stores the spatial information of the superimposed object.

At Step S126, the control unit 29 determines whether or not an instruction to end generation processing and storage processing for spatial information of a superimposed object has been input. If the control unit 29 determines that the instruction to end generation processing and storage processing for spatial information of a superimposed object has not been input (Step S126: No), the control unit 29 advances the processing to Step S121, and repeats the above described generation processing and storage processing for spatial information of a superimposed object. On the contrary, if the control unit 29 determines that the instruction to end generation processing and storage processing for spatial information of a superimposed object has been input (Step S126: Yes), the control unit 29 ends the generation processing and storage processing for the spatial information of the superimposed object.

Further, in parallel with the above described generation processing for spatial information of a superimposed object, the object superimposing unit 27 performs the above described superimposition processing for a superimposed object (Steps S111 to S116).

According to this second modified example, since, when spatial information of a superimposed object generated by the superimposed object information generating unit 23 is generated by use of a subject image newer than that corresponding to spatial information of a superimposed object that has been stored in the superimposed object information storage unit 282, the control unit 29 stores the generated spatial information in the superimposed object information storage unit 282; the latest spatial information of the superimposed object that is newly stored in the superimposed object information storage unit 282 is that of the latest subject image. Thereby, the spatial information of the superimposed object is constantly updated based on the latest subject image, and thus superimposition processing can be even more accurately performed.

In contrast, when spatial information of a superimposed object is generated by use of plural threads like in the above described first modified example, if shapes and sizes of a location of interest are different between detection target images, time periods required for generation processing for the superimposed objects vary. Depending on detection target images, for which spatial information of superimposed objects are being generated in overlapping time periods between threads, the order of times of completion of the generation of the spatial information of the superimposed objects may be reversed from the order of times of start of the generation. According to this second modified example, the time of acquisition of a detection target image corresponding to spatial information of a superimposed object that has been stored in the superimposed object information storage unit 282 is able to be made the latest.

Third Modified Example of First Embodiment

Figure 9:
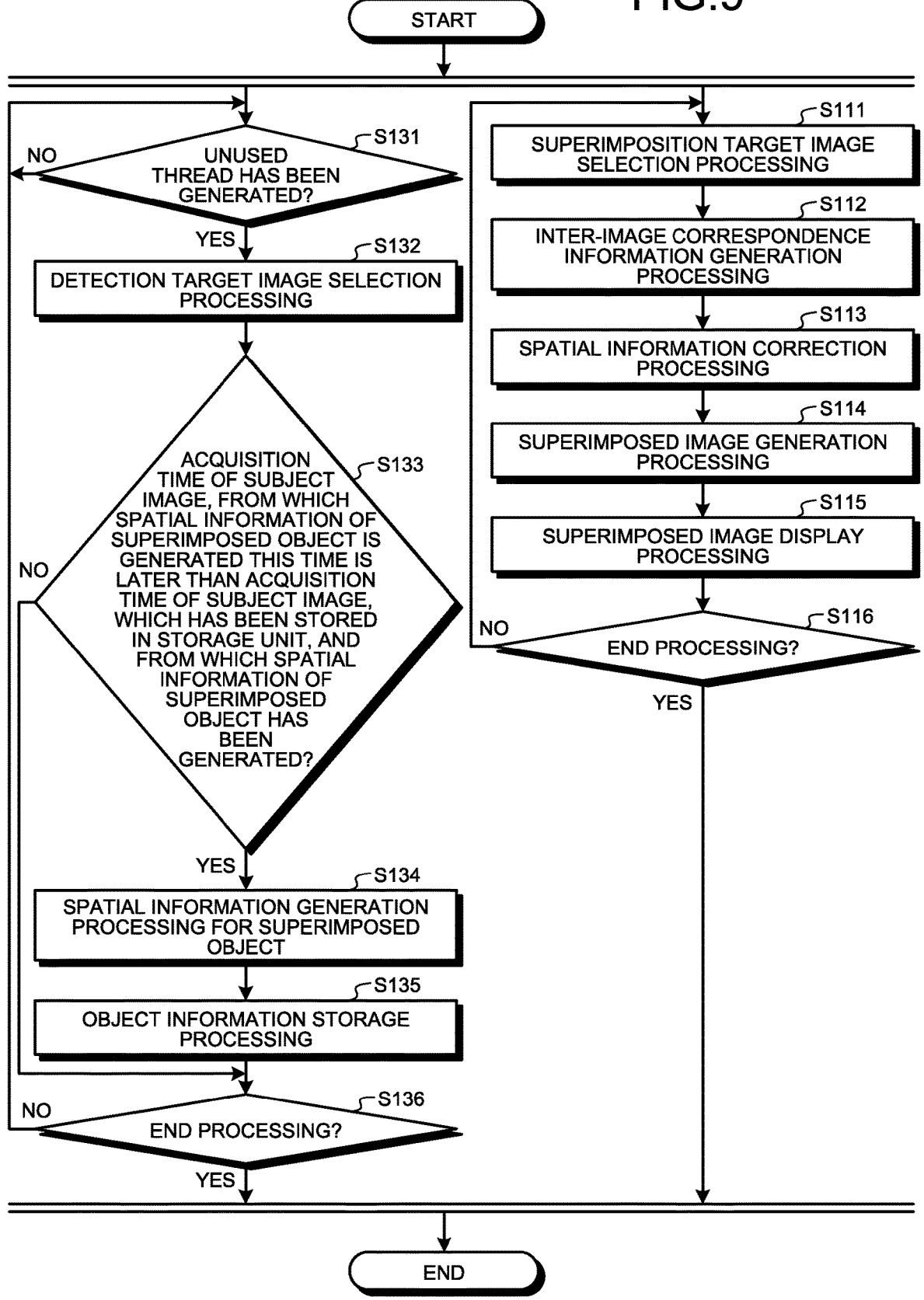
FIG. 9 is a flow chart depicting an outline of superimposition processing for a superimposed object, the superimposition processing being performed by an image processing apparatus according to a third modified example of the first embodiment of the present disclosure.

In this third modified example, comparison between times of acquisition of detection target images is performed before generation of spatial information of superimposed objects. FIG. 9 is a flow chart depicting an outline of superimposition processing for a superimposed object performed by an image processing apparatus according to the third modified example of the first embodiment of the present disclosure. Hereinafter, description will be made on the assumption that each unit operates under control by the control unit 29. In the processing performed by the image processing apparatus 2 according to this third modified example, processing for generation of spatial information of a superimposed object (Steps S131 to S136) and processing for superimposition of a superimposed object on a superimposition target image (Steps S111 to S116) are performed in parallel.

First, the control unit 29 determines whether or not any unused thread usable in generation of spatial information of a superimposed object has been generated (Step S131). If the control unit 29 determines that any unused thread has not been generated (Step S131: No), the control unit 29 repeats checking whether or not any unused thread has been generated. On the contrary, if the control unit 29 determines that an unused thread has been generated (Step S131: Yes), the processing is advanced to Step S132.

At Step S132, the detection target image selecting unit 22 selects a detection target image, from which a location of interest is to be detected. The detection target image selecting unit 22 selects a subject image serving as the detection target image, from the subject images that have been acquired by the image acquiring unit 21 and stored in the subject image storage unit 281.

At Step S133, the control unit 29 compares a time of acquisition of the detection target image, from which spatial information of a superimposed object is to be generated by the superimposed object information generating unit 23 (hereinafter, referred to as a third acquisition time), with the above described second acquisition time. If the third acquisition time is earlier than the second acquisition time (Step S133: No), the control unit 29 advances the processing to Step S136. On the contrary, if the third acquisition time is later than the second acquisition time (Step S133: Yes), the control unit 29 advances the processing to Step S134.

At Step S134, the superimposed object information generating unit 23 generates, from the detection target image, spatial information of any superimposed object to be superimposed on a superimposition target image input from the image acquiring unit 21.

At Step S135 subsequent to Step S134, the superimposed object information storage unit 282 stores the spatial information generated by the superimposed object information generating unit 23. After the superimposed object information storage unit 282 stores the spatial information of the superimposed object, the control unit 29 advances the processing to Step S136.

At Step S136, the control unit 29 determines whether or not an instruction to end generation processing and storage processing for spatial information of a superimposed object has been input. If the control unit 29 determines that the instruction to end generation processing and storage processing for spatial information of a superimposed object has not been input (Step S136: No), the control unit 29 advances the processing to Step S131, and repeats the above described generation processing and storage processing for spatial information of a superimposed object. On the contrary, if the control unit 29 determines that the instruction to end generation processing and storage processing for spatial information of a superimposed object has been input (Step S136: Yes), the control unit 29 ends the generation processing and storage processing for the spatial information of the superimposed object.

Further, in parallel with the above described generation processing for spatial information of a superimposed object, the object superimposing unit 27 performs the above described superimposition processing for a superimposed object (Step S111 to Step S116).

According to this third modified example, since, when a detection target image, from which spatial information of a superimposed object is to be generated by the superimposed object information generating unit 23, is newer than a detection target image corresponding to spatial information of a superimposed object that has been stored in the superimposed object information storage unit 282, the control unit 29 generates spatial information of a superimposed object; spatial information of a superimposed object that is newly stored in the superimposed object information storage unit 282 is that of the latest subject image. Thereby, update to spatial information of a superimposed object based on the latest subject image is constantly performed, the spatial information of a superimposed object is constantly updated based on the latest subject image, and thus superimposition processing can be more accurately performed. Further, according to this third modified example, since unnecessary spatial information of a superimposed object is not generated, the load of calculation processing may be reduced as compared to that in the above described second modified example.

Fourth Modified Example of First Embodiment

In this fourth modified example, information detected by a sensor is acquired, and spatial information of a superimposed object is generated by detection of a location of interest based on the information detected by the sensor.

Figure 10:
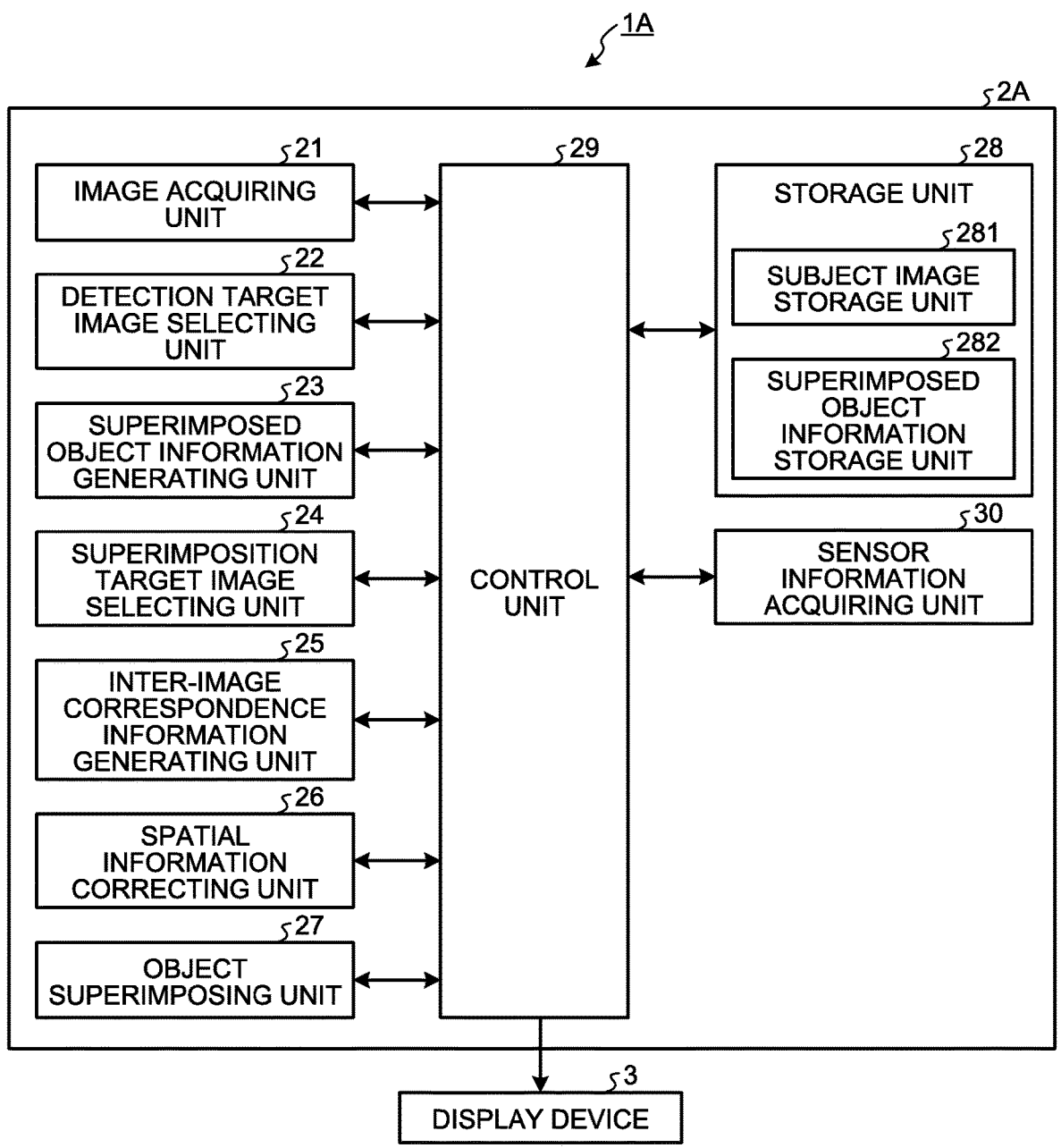
FIG. 10 is a block diagram depicting a functional configuration of an image processing system according to a fourth modified example of the first embodiment of the present disclosure.

FIG. 10 is a block diagram depicting a functional configuration of an image processing system according to the fourth modified example of the first embodiment of the present disclosure. An image processing system 1A according to this modified example includes an image processing apparatus 2A, and the display device 3. In addition to the above described configuration of the image processing apparatus 2, the image processing apparatus 2A includes a sensor information acquiring unit 30.

The sensor information acquiring unit 30 acquires detected information from an external sensor, for example, an infrared sensor or a laser distance measuring device, and inputs sensor information including positional information of a location of interest, to the superimposed object information generating unit 23.

When the superimposed object information generating unit 23 acquires the sensor information including the positional information of the location of interest from the sensor information acquiring unit 30, the superimposed object information generating unit 23 generates, based on the positional information in the sensor information, spatial information of a superimposed object to be superimposed on the location of interest in a superimposition target image, the superimposed object being an object specifying the location of interest.

Thereafter, similarly to the first embodiment, the superimposition target image selecting unit 24 selects a superimposition target image to be displayed on the display device 3, and the inter-image correspondence information generating unit 25 generates inter-image correspondence information that is information indicating estimated correspondence between: the detection target image used by the superimposed object information generating unit 23 in generating the superimposed object; and the superimposition target image selected by the superimposition target image selecting unit 24. Thereafter, the spatial information correcting unit 26 corrects the spatial information of the superimposed object, based on the inter-image correspondence information. The object superimposing unit 27 superimposes the superimposed object that has been corrected by the spatial information correcting unit 26, on the superimposition target image.

According to this fourth modified example, similarly to the above described first embodiment, even when a superimposed object detected from a detection target image for the superimposed object is superimposed on a superimposition target image temporally different from that detection target image, positional displacement of the superimposed object in relation to a position of a location of interest in the superimposition target image is able to be reduced. Therefore, subject images sequentially acquired by the image acquiring unit 21, as the superimposition target image, may be displayed on the display device 3 with the superimposed objects being superimposed thereon, and with reduced positional displacement.

Second Embodiment

Figure 11:
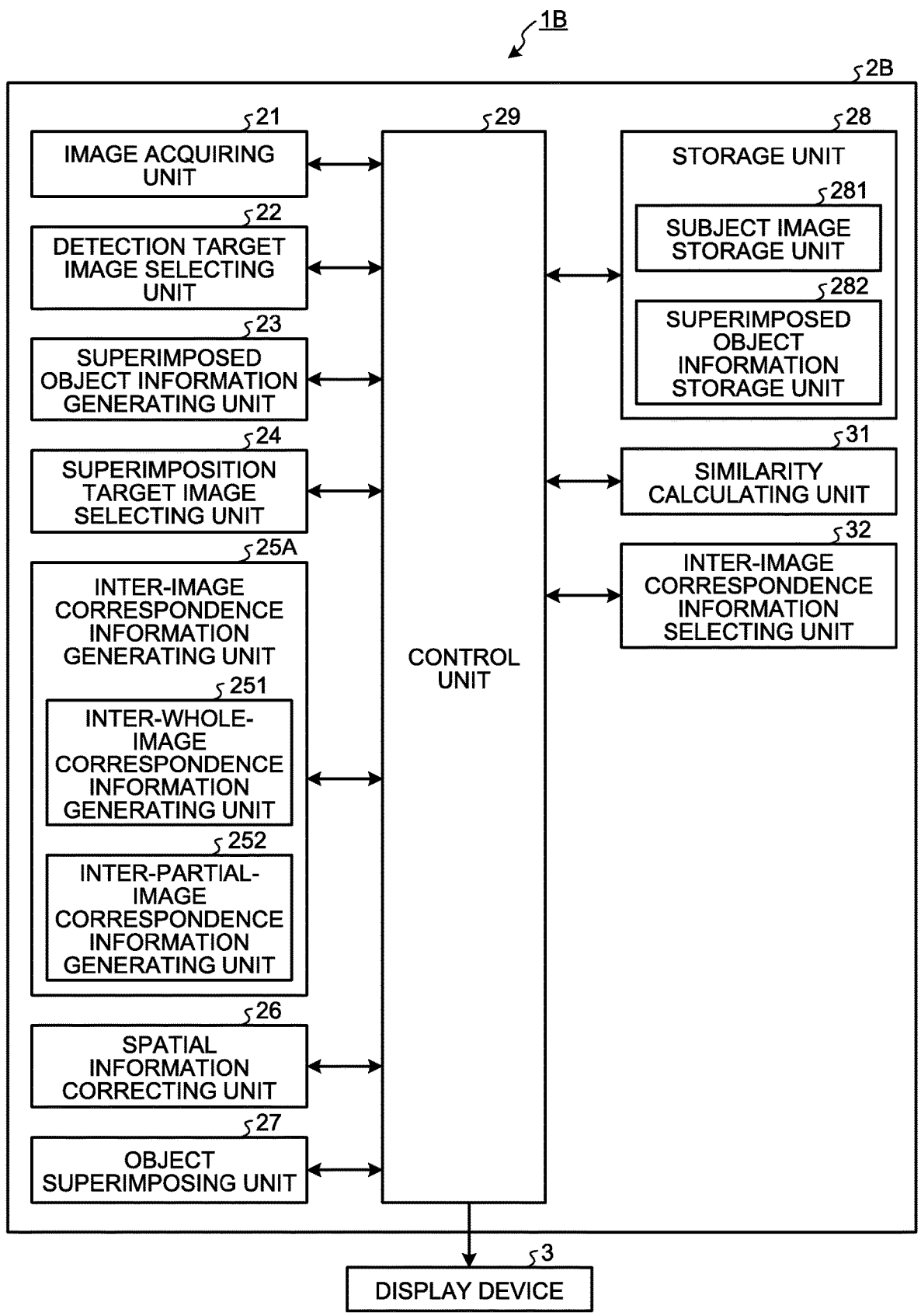
FIG. 11 is a block diagram depicting a functional configuration of an image processing apparatus according to a second embodiment of the present disclosure.

In this second embodiment, inter-image correspondence information between a detection target image and a superimposition target image for the whole areas thereof and for partial areas thereof are generated, and either one of these is selected. FIG. 11 is a block diagram depicting a functional configuration of an image processing system according to the second embodiment of the present disclosure. An image processing system 1B according to this second embodiment includes an image processing apparatus 2B, and the display device 3. The image processing apparatus 2B includes, in contrast to the above described configuration of the image processing apparatuses 2, 2A, an inter-image correspondence information generating unit 25A, instead of the inter-image correspondence information generating unit 25. The inter-image correspondence information generating unit 25A has an inter-whole-image correspondence information generating unit 251, and an inter-partial-image correspondence information generating unit 252.

The inter-whole-image correspondence information generating unit 251 generates inter-whole-image correspondence information between a detection target image and a superimposition target image. The detection target image is a subject image, from which the superimposed object information generating unit 23 is to generate spatial information of a superimposed object. The superimposition target image is a subject image that has been determined by the superimposition target image selecting unit 24 as a target, on which a superimposed object is to be superimposed. The inter-whole-image correspondence information is expressed by coordinate transformation generated by use of the whole area of the detection target image.

The inter-partial-image correspondence information generating unit 252 generates inter-partial-image correspondence information between the detection target image and the superimposition target image. The inter-partial-image correspondence information is expressed by coordinate transformation generated by use of a partial area corresponding to an area where the superimposed object is to be placed in the detection target image.

A similarity calculating unit 31 calculates: an inter-whole-image similarity (a first similarity) between a first object area corresponding to a superimposition object in the detection target image, and a second object area in the superimposition target image, the second object area being associated with the first object area by use of the inter-whole-image correspondence information (transformation parameters); and an inter-partial-image similarity (a second similarity) between the first object area, and a third object area in the superimposition target image, the third object area being associated with the first object area by use of the inter-partial-image correspondence information (transformation parameters). A similarity calculated by the similarity calculating unit 31 may be a known sum of absolute differences (SAD) or a sum of squared differences (SSD), or may be calculated by normalized cross-correction (NCC). The SAD and SSD are values representing dissimilarity, and when they are used as similarities, the magnitude correlation is reversed. That is, the larger the dissimilarity is, the smaller the similarity becomes.

An inter-image correspondence information selecting unit 32 selects, based on the inter-whole-image similarity and the inter-partial-image similarity that have been calculated by the similarity calculating unit 31, one of the inter-whole-image correspondence information and the inter-partial-image correspondence information, as inter-image correspondence information. In this embodiment, the inter-image correspondence information selecting unit 32 selects the inter-image correspondence information corresponding to the larger one of the inter-whole-image similarity and the inter-partial-image similarity.

Figure 12:
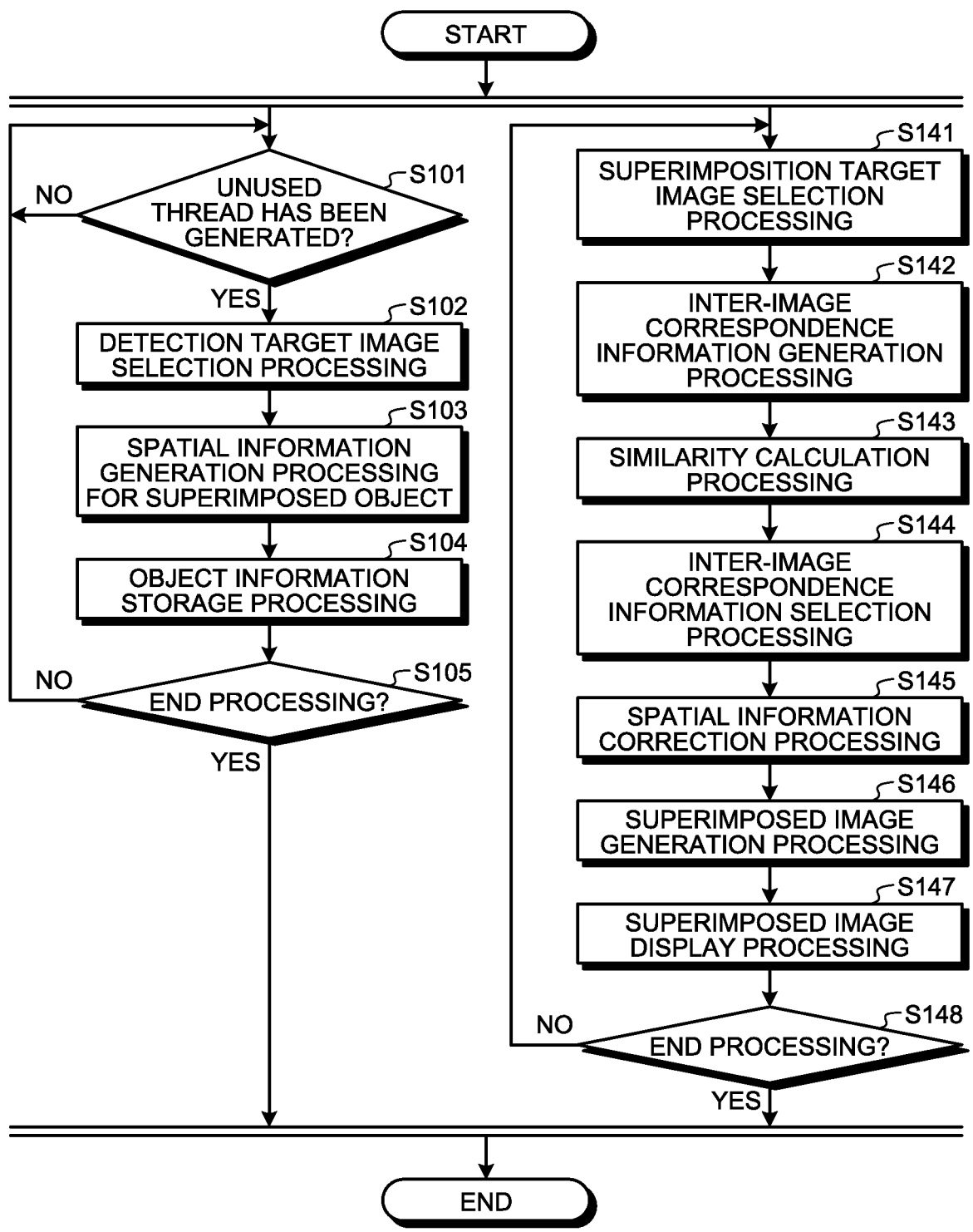
FIG. 12 is a flow chart depicting an outline of superimposition processing for a superimposed object, the superimposition processing being performed by an image processing apparatus according to the second embodiment of the present disclosure.

Next, object superimposition processing performed by the units of the image processing apparatus 2B will be described by reference to the drawings. FIG. 12 is a flow chart for explanation of an outline of superimposition processing for a superimposed object performed by the image processing apparatus according to the second embodiment of the present disclosure. Hereinafter, description will be made on the assumption that each unit operates under control by the control unit 29. In the processing performed by the image processing apparatus 2B, processing for generation of spatial information of a superimposed object (Steps S101 to S105) and processing for superimposition of a superimposed object on a superimposition target image (Steps S141 to S148) are performed in parallel.

First, similarly to the above described first embodiment, the control unit 29 generates spatial information of a superimposed object, and stores the generated spatial information of the superimposed object in the superimposed object information storage unit 282 (Steps S101 to S105).

In parallel with the above described generation processing for the spatial information of the superimposed object, the control unit 29 performs superimposition processing for a superimposed object. First, the superimposition target image selecting unit 24 selects a superimposition target image (for example, the above described subject image $W_{12}$) to be displayed on the display device 3 with a superimposed object superimposed thereon (Step S141).

At Step S142 subsequent to Step S141, the inter-image correspondence information generating unit 25A refers to the superimposed object information storage unit 282 and acquires a detection target image corresponding to the latest spatial information of a superimposed object, and generates inter-image correspondence information, which is expressed by coordinate transformation, between the acquired detection target image and the superimposition target image selected by the superimposition target image selecting unit 24. At this Step S142, the inter-whole-image correspondence information generating unit 251 generates the above described inter-whole-image correspondence information, and the inter-partial-image correspondence information generating unit 252 generates the above described inter-partial-image correspondence information.

At Step S143 subsequent to Step S142, the similarity calculating unit 31 calculates the above described inter-whole-image similarity and inter-partial-image similarity. At Step S144 thereafter, the inter-image correspondence information selecting unit 32 selects, based on the inter-whole-image similarity and inter-partial-image similarity calculated by the similarity calculating unit 31, either one of the inter-whole-image correspondence information and inter-partial-image correspondence information, as inter-image correspondence information.

At Step S145 subsequent to Step S144, the spatial information correcting unit 26 performs spatial information correction based on transformation parameters of the inter-image correspondence information selected by the inter-image correspondence information selecting unit 32.

At Step S146 subsequent to Step S145, the object superimposing unit 27 generates a superimposed object having the spatial information that has been corrected by the spatial information correcting unit 26, and generates a superimposed image by superimposing this superimposed object on the superimposition target image. The object superimposing unit 27 generates, for example, as depicted in FIG. 3, the superimposed image $W_{s1}$ having the parts of the lesion sites $S_{11}$ and $S_{12}$ surrounded by the superimposed objects $Q_{11}$ and $Q_{12}$.

At Step S147 subsequent to Step S146, under control by the control unit 29, the superimposed image that has been generated by the object superimposing unit 27 is displayed on the display device 3. After displaying the superimposed image on the display device 3, the control unit 29 advances the processing to Step S148.

At Step S148, the control unit 29 determines whether or not an instruction to end the superimposition processing for a superimposed object has been input. If the control unit 29 determines that the instruction to end the superimposition processing for a superimposed object has not been input (Step S148: No), the control unit 29 advances the processing to Step S141, and repeats the above described superimposition processing for a superimposed object. On the contrary, if the control unit 29 determines that the instruction to end the superimposition processing for a superimposed object has been input (Step S148: Yes), the control unit 29 ends the superimposition processing for the superimposed object.

Similarly to the above described first embodiment, in the object superimposition processing according to this second embodiment also, by repeatedly using, with respect to the subject images sequentially input to the image processing apparatus 2, the latest spatial information of a superimposed object, that has been stored in the superimposed object information storage unit 282, superimposed objects are respectively superimposed on plural superimposition target images selected by the superimposition target image selecting unit 24.

According to the above described second embodiment, the inter-image correspondence information generating unit 25A generates plural pieces of inter-image correspondence information for different areas of a subject image, the similarity calculating unit 31 calculates a similarity for each of the plural pieces of inter-image correspondence information, and the inter-image correspondence information selecting unit 32 selects one of the plural pieces of inter-image correspondence information by using the calculated similarities. Thereby, when an area corresponding to a superimposed object moves in association with the whole image, spatial information thereof may be corrected accurately even if information on the area is scarce; and when an area corresponding to a superimposed object and the whole image move differently, since spatial information thereof is corrected by use of inter-image correspondence information for the area, the spatial information may be corrected even more accurately.

Third Embodiment

In this third embodiment, the superimposed object information generating unit 23 generates inter-image correspondence information, which is expressed by coordinate transformation, with respect to subject images sequentially input, and performs processing of accumulating the inter-image correspondence information as coordinate transformation information between adjacent frames in the storage unit 28.

Figure 13:
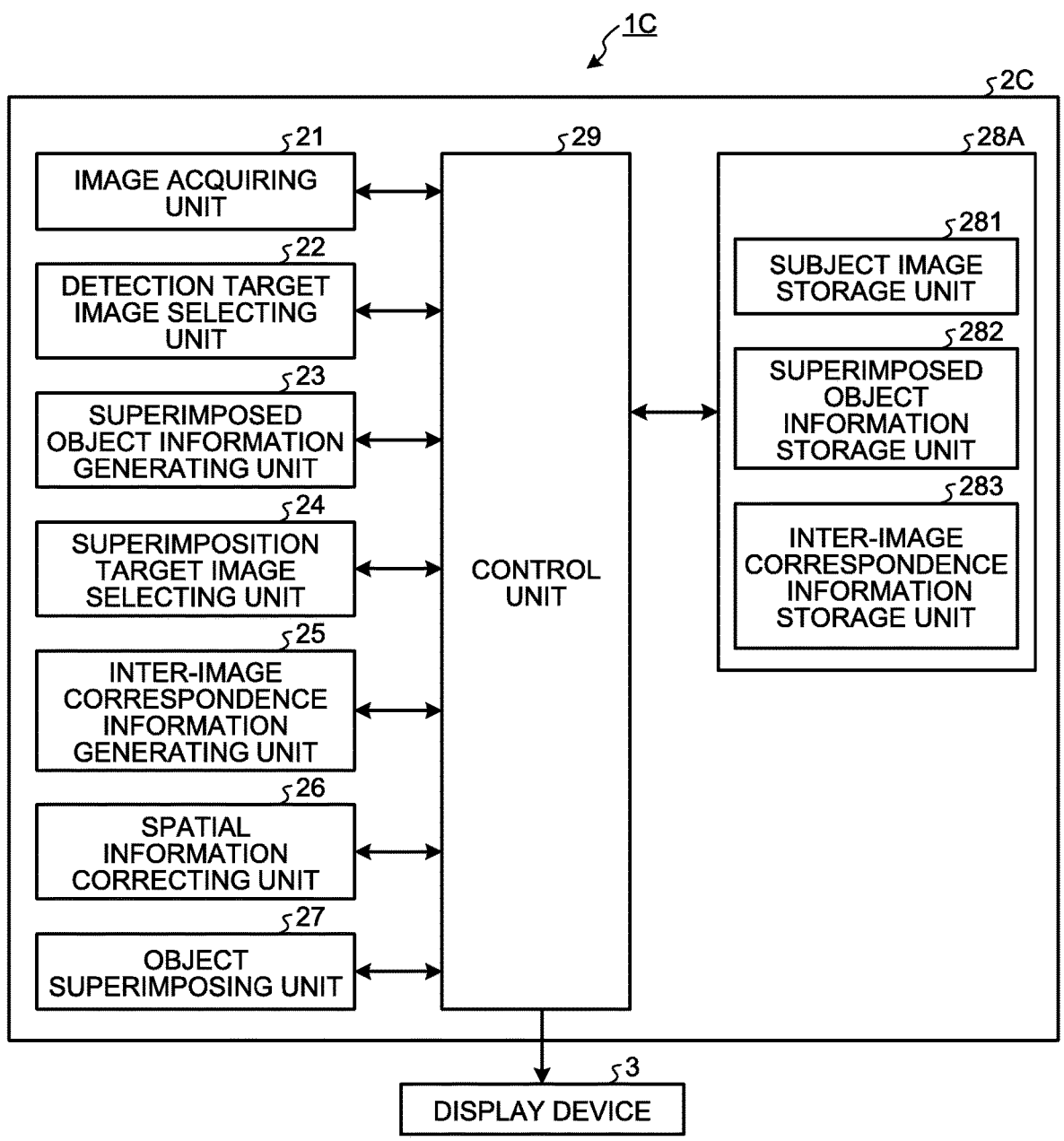
FIG. 13 is a block diagram depicting a functional configuration of an image processing system according to a third embodiment of the present disclosure.

FIG. 13 is a block diagram depicting a functional configuration of an image processing system according to the third embodiment of the present disclosure. An image processing system 1C according to this third embodiment includes an image processing apparatus 2C, and the display device 3. The image processing apparatus 2C includes, instead of the above described storage unit 28 of the image processing apparatus 2, a storage unit 28A. The storage unit 28A has the subject image storage unit 281, the superimposed object information storage unit 282, and an inter-image correspondence information storage unit 283.

In this third embodiment, the inter-image correspondence information generating unit 25 generates the inter-image correspondence information, which is information between subject images temporally adjacent to each other, and sequentially accumulates the inter-image correspondence information in the inter-image correspondence information storage unit 283. The inter-image correspondence information is information between, for example, a subject image based on an image signal input from the image acquiring unit 21, and a subject image that is prior to that subject image by one frame. Examples of subject images that are temporally adjacent to each other include: subject images that have been extracted by thinning out processing or the like from plural subject images sequentially acquired and that are intermittently adjacent to each other; and a combination of subject images that are other than those adjacent to each other in terms of times of actual acquisition of the subject images.

Further, when inter-image correspondence information related to correspondence between a detection target image, from which a superimposed object has been detected by the superimposed object information generating unit 23, and a superimposition target image that has been selected by the superimposition target image selecting unit 24, is generated: inter-image correspondence information related to correspondence between a subject image, from which a superimposed object has been detected by the superimposed object information generating unit 23, and a subject image that has been selected by the superimposition target image selecting unit 24, is generated by the inter-image correspondence information generating unit 25 by referring to coordinate information that is spatial information of the superimposed object generated by the superimposed object information generating unit 23 and one or plural pieces of inter-image correspondence information that has been accumulated in the inter-image correspondence information storage unit 283; and accumulating the inter-image correspondence information.

As described above, in this third embodiment, for plural subject images present between the subject image $W_{11}$ that is a detection target image, and the subject image $W_{12}$ that is a superimposition target image, pieces of inter-image correspondence information for subject images temporally adjacent to each other are respectively generated, the pieces of inter-image correspondence information not being generated in the above described first and second embodiments.

Figure 14:
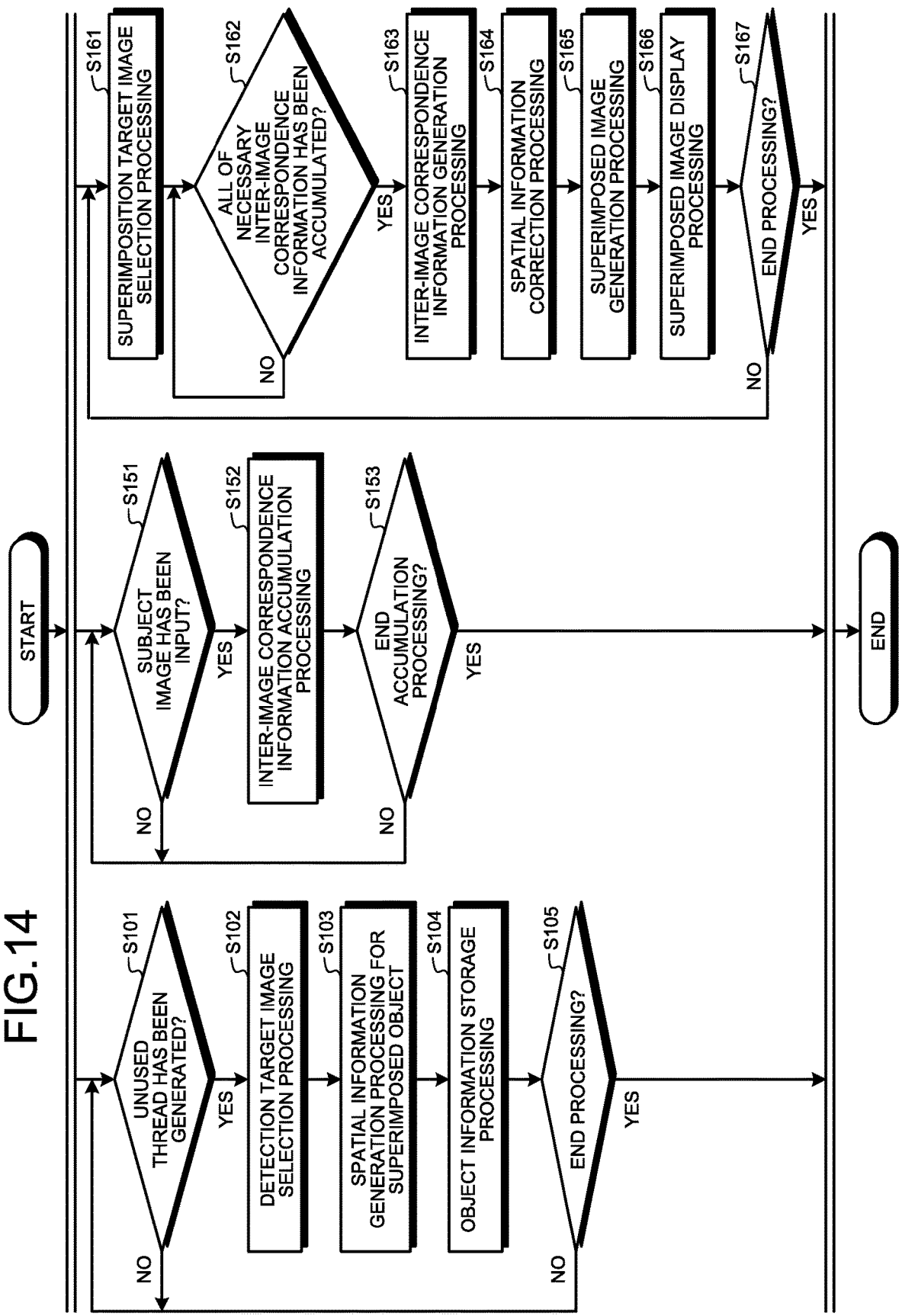
FIG. 14 is a flow chart depicting an outline of superimposition processing for a superimposed object, the superimposition processing being performed by an image processing apparatus according to the third embodiment of the present disclosure.

Next, processing performed by the units of the image processing apparatus 2C will be described by reference to the drawings. FIG. 14 is a flow chart for explanation of an outline of superimposition processing for a superimposed object performed by the image processing apparatus according to the third embodiment of the present disclosure. Hereinafter, description will be made on the assumption that each unit operates under control by the control unit 29. In the processing performed by the image processing apparatus 2C, processing for generation of spatial information of a superimposed object (Steps S101 to S105), generation processing for inter-image correspondence information (Steps S151 to S153), and processing for superimposition of a superimposed object on a superimposition target image (Steps S161 to S167) are performed in parallel.

First, similarly to the above described first embodiment, the control unit 29 generates spatial information of a superimposed object, and stores the generated spatial information of the superimposed object in the superimposed object information storage unit 282 (Steps S101 to S105).

In parallel with the above described generation processing for the spatial information of the superimposed object, the control unit 29 determines whether or not a subject image has been input (Step S151). If the control unit 29 determines that a subject image has not been input (Step S131: No), the control unit 29 repeats checking for any input of a subject image. On the contrary, if the control unit 29 determines that a subject image has been input (Step S151: Yes), the processing is advanced to Step S152.

At Step S152, the inter-image correspondence information generating unit 25 generates inter-image correspondence information between a subject image based on an image signal input from the image acquiring unit 21 and a subject image that has been stored in the subject image storage unit 281 and that is of a time adjacent to that of the subject image input from the image acquiring unit 21, and sequentially accumulates the inter-image correspondence information in the inter-image correspondence information storage unit 283.

Thereafter, the control unit 29 determines whether or not an instruction to end the accumulation processing for inter-image correspondence information has been input (Step S153). If the control unit 29 determines that the instruction to end the accumulation processing has not been input (Step S153: No), the control unit 29 returns to Step S151 and repeats the above described accumulation processing. On the contrary, if the control unit 29 determines that the instruction to end the accumulation processing has been input (Step S153: Yes), the control unit 29 ends the accumulation processing. Input of the instruction to end the accumulation processing for inter-image correspondence information may be input of a signal input via an input device not depicted in the drawings, or it may be determined that the instruction to end the accumulation processing has been input when a subject image has not been newly input even after elapse of a predetermined time period from the last input of a subject image.

Further, in parallel with the above described generation processing for spatial information of a superimposed object and accumulation processing for inter-image correspondence information, the control unit 29 performs superimposition processing for a superimposed object. First, the superimposition target image selecting unit 24 selects a superimposition target image (for example, the above described subject image $W_{12}$) to be displayed on the display device 3 with a superimposed object superimposed thereon (Step S161).

At Step S162 subsequent to Step S161, the inter-image correspondence information generating unit 25 acquires one or plural pieces of inter-image correspondence information that has been accumulated in the inter-image correspondence information storage unit 283, and sequentially accumulates the inter-image correspondence information. The inter-image correspondence information generating unit 25 determines whether or not accumulation processing for all of required inter-image correspondence information has been finished every time accumulation is performed, and if the inter-image correspondence information generating unit 25 determines that the accumulation processing for all of required inter-image correspondence information has not been finished (Step S162: No), the inter-image correspondence information generating unit 25 refers to the inter-image correspondence information storage unit 283 and acquires inter-image correspondence information. On the contrary, if the inter-image correspondence information generating unit 25 determines that the accumulation of all of the required inter-image correspondence information has been finished (Step S162: Yes), the inter-image correspondence information generating unit 25 advances the processing to Step S163.

At Step S163, the inter-image correspondence information generating unit 25 determines, as inter-image correspondence information, information acquired as a result of the accumulation of the inter-image correspondence information in Step S162.

At Step S164 subsequent to Step S163, the spatial information correcting unit 26 performs spatial information correction based on transformation parameters of the inter-image correspondence information generated by the inter-image correspondence information generating unit 25.

At Step S165 subsequent to Step S164, the object superimposing unit 27 generates a superimposed object having the spatial information that has been corrected by the spatial information correcting unit 26, and generates a superimposed image by superimposing this superimposed object on the superimposition target image.

At Step S166 subsequent to Step S165, under control by the control unit 29, the superimposed image generated by the object superimposing unit 27 is displayed on the display device 3. After displaying the superimposed image on the display device 3, the control unit 29 advances the processing to Step S167.

At Step S167, the control unit 29 determines whether or not an instruction to end the superimposition processing for a superimposed object has been input. If the control unit 29 determines that the instruction to end the superimposition processing for a superimposed object has not been input (Step S167: No), the control unit 29 advances the processing to Step S161, and repeats the above described superimposition processing for a superimposed object. On the contrary, if the control unit 29 determines that the instruction to end the superimposition processing for a superimposed object has been input (Step S167: Yes), the control unit 29 ends the processing.

According to the above described third embodiment, for subject images that are sequentially input, the inter-image correspondence information generating unit 25 generates inter-image correspondence information and accumulates the inter-image correspondence information as inter-image correspondence information, in the storage unit 28A; the inter-image correspondence information generating unit 25 generates inter-image correspondence information between a detection target image and a superimposition target image by accumulating inter-image correspondence information generated between the detection target image and the superimposition target image; and spatial information of a superimposed object is corrected. Thereby, inter-image correspondence information may be generated in consideration of movement in subject images present between a detection target image and a superimposition target image, and a superimposed object may be superimposed more certainly in a position of a location of interest in the superimposition target image.

Fourth Embodiment

Figure 15:
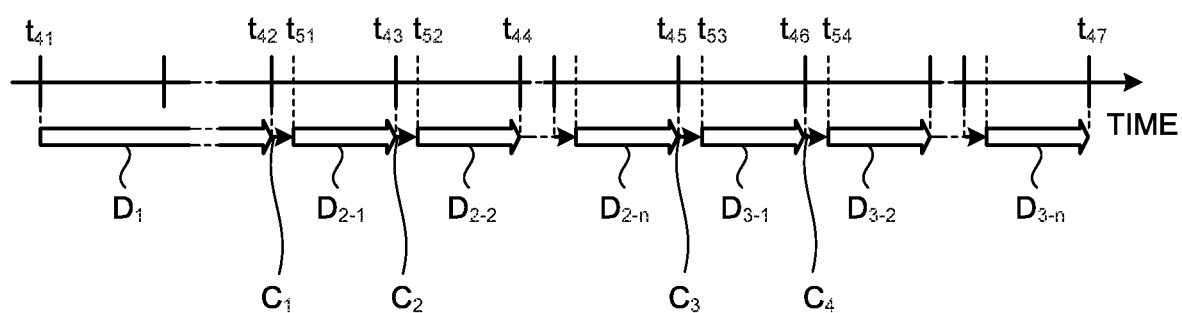
FIG. 15 is a diagram for explanation of an outline of superimposition processing for a superimposed object, the superimposition processing being performed by an image processing apparatus according to a fourth embodiment of the present disclosure.

In this fourth embodiment, the superimposed object information generating unit 23 and the object superimposing unit 27 alternately perform processing by using one thread. Description will be made on the assumption that a configuration of an image processing apparatus according to this fourth embodiment is the same as that of the above described image processing apparatus 2 according to the first embodiment. FIG. 15 is a diagram for explanation of an outline of superimposition processing for a superimposed object performed by the image processing apparatus according to the fourth embodiment of the present disclosure. Description will be made on the assumption that in FIG. 15, a new subject image is acquired at each of times $t_{42}$, $t_{43}$, $t_{44}$, $t_{45}$, $t_{46}$, and $t_{47}$. For example, a time period between the time $t_{42}$ and the time $t_{43}$ corresponds to a time period, in which a subject image of one frame is input.

First, the superimposed object information generating unit 23 executes, in a time period from the time $t_{41}$ to the time $t_{42}$, spatial information generation processing $D_1$ that is generation processing for spatial information of a superimposed object, from the latest subject image at the time $t_{41}$, and stores the generated spatial information of the superimposed object in the storage unit 28. This spatial information generation processing $D_1$ requires a time period, in which subject images of several frames are input.

Thereafter, by superimposed object superimposition processing $C_1$ executed in a time period from the time $t_{42}$ to the time $t_{43}$, the object superimposing unit 27 performs object superimposition processing based on the spatial information of the superimposed object generated by the spatial information generation processing $D_1$. This superimposition processing for the superimposed object requires, for example, a time period, in which a subject image of 0.1 frames is input.

In the superimposed object superimposition processing $C_1$, with the subject image acquired at the time $t_{42}$ being a superimposition target image, object superimposition processing is performed based on the spatial information of the superimposed object generated by the spatial information generation processing $D_1$. The control unit 29 displays a superimposed image generated by the superimposed object superimposition processing $C_1$, on the display device 3.

In a time period from a time $t_{51}$, at which the superimposed object superimposition processing $C_1$ is finished, to the time $t_{43}$, that is, in a time period of 0.9 frame, spatial information generation processing $D_{2-1}$ that is generation processing for spatial information of a superimposed object of the subject image acquired at the time $t_{42}$ is executed. The spatial information of the superimposed object generated by the spatial information generation processing $D_{2-1}$ is a part of spatial information of a superimposed object generated from the subject image acquired at the time $t_{42}$.

Thereafter, by superimposed object superimposition processing $C_2$ executed in a time period from the time $t_{43}$ to the time $t_{44}$, the object superimposing unit 27 performs object superimposition processing based on the spatial information of the superimposed object generated by the spatial information generation processing $D_1$. In the superimposed object superimposition processing $C_2$, with the subject image acquired at the time $t_{43}$ being a superimposition target image, object superimposition processing is performed based on the spatial information of the superimposed object generated by the spatial information generation processing $D_1$. The control unit 29 displays a superimposed image generated by the superimposed object superimposition processing $C_2$, on the display device 3.

In a time period of 0.9 frames from a time $t_{52}$, at which the superimposed object superimposition processing $C_2$ is finished, to the time $t_{44}$, spatial information generation processing $D_{2-2}$ that is generation processing for spatial information of a superimposed object of the subject image acquired at the time $t_{42}$ is executed. The spatial information of the superimposed object generated by the spatial information generation processing $D_{2-2}$ is a part of spatial information of a superimposed object generated subsequently to the spatial information generation processing $D_{2-1}$.

Thereinafter, the superimposed object information generating unit 23 performs the spatial information generation processing a predetermined number of times up to the spatial information generation processing $D_{2-n}$, thereby to complete the generation processing for the spatial information of the superimposed object of the subject image acquired at the time $t_{42}$, while the superimposition processing is performed, based on the spatial information of the superimposed object generated by the spatial information generation processing $D_1$, with respect to the subject images serving as the superimposition target images acquired at each time. Depending on the subject image, the time period required for the last generation processing for spatial information of a superimposed object may be shorter than the time period of 0.9 frames. In this case, the superimposed object information generating unit 23 waits until a new subject image is acquired.

After the generation processing for the spatial information of the superimposed object of the subject image acquired at the time $t_{42}$ is finished, the object superimposing unit 27 performs, by superimposed object superimposition processing $C_3$ executed in a time period from the time $t_{45}$ to the time $t_{53}$, the object superimposition processing, based on the spatial information of the superimposed object generated by the spatial information generation processing $D_{2-1}$ to $D_{2-n}$. In the superimposed object superimposition processing $C_3$, with the subject image acquired at the time $t_{45}$ being a superimposition target image, the object superimposition processing is performed based on the spatial information of the superimposed object generated by the spatial information generation processing $D_{2-1}$ to $D_{2-n}$. The control unit 29 displays a superimposed image generated by the superimposed object superimposition processing $C_3$, on the display device 3.

Thereafter, in a time period of 0.9 frames from a time $t_{53}$, at which the superimposed object superimposition processing $C_3$ is finished, to the time $t_{46}$, spatial information generation processing $D_{3-1}$ that is generation processing for spatial information of the superimposed object of the subject image acquired at the time $t_{45}$ is executed. The spatial information of the superimposed object generated by the spatial information generation processing $D_{3-1}$ is a part of the spatial information of the superimposed object generated from the subject image acquired at the time $t_{45}$. Thereafter, similarly to the spatial information generation processing $D_{2-2}$ to $D_{2-n}$, the superimposed object information generating unit 23 performs the spatial information generation processing $D_{3-2}$ through $D_{3-n}$ thereby to complete the generation processing for the spatial information of the superimposed object of the subject image acquired at the time $t_{45}$, while the superimposition processing is time-divisionally performed, based on the spatial information of the superimposed object generated by the spatial information generation processing $D_{2-1}$ through $D_{2-n}$, with respect to the subject image serving as the superimposition target image acquired at each time.

Thereafter, a superimposed image having a superimposed object superimposed thereon is generated while, similarly to the above described spatial information generation processing $D_{2-2}$ to $D_{2-n}$ and $D_{3-2}$ to $D_{3-n}$, for example, spatial information of a superimposed object is time-divisionally generated from the subject image acquired at the time $t_{47}$.

According to this fourth embodiment, in a case where a thread for generation of spatial information of a superimposed object and a thread for superimposition processing for a superimposed object form a common thread, spatial information of a superimposed object is generated time-divisionally, and information having a superimposed object superimposed on a superimposition target image is generated by use of the superimposed object's spatial information that has been generated already. Thereby, even in a case where a superimposed object detected from a detection target image for the superimposed object is superimposed on a superimposition target image that is temporally different from the detection target image; positional displacement of the superimposed object in relation to a position of a location of interest in the superimposition target image may be reduced, and subject images sequentially acquired by the image acquiring unit 21 may be displayed on the display device 3 with the superimposed objects being superimposed thereon, and with reduced positional displacement.

The present disclosure is not limited to the above described embodiments and modified example as-is, and upon implementation of the present disclosure, without departing from the gist of the disclosure, components thereof may be modified. Further, by combination of plural components disclosed with respect to the above described embodiments as appropriate, various embodiments may be formed. For example, some components may be eliminated from the components described above in the embodiments and modified examples. Further, the components described in the embodiments and modified examples may be combined as appropriate.

As described above, the present disclosure may include various embodiments and the like not described herein, and design changes and the like may be performed without departing from the technical ideas stated in the claims, as appropriate.

The present disclosure has an effect of enabling, even in a case where an object specifying a location of interest is superimposed on an image different from an image, from which the object has been generated: reduction of positional displacement between the location of interest in the superimposed image and the object; and improvement in update frequency of the object.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

The image processing apparatus and the like according to the present embodiment may include a processor and a storage (e.g., a memory). The functions of individual units in the processor may be implemented by respective pieces of hardware or may be implemented by an integrated piece of hardware, for example. The processor may include hardware, and the hardware may include at least one of a circuit for processing digital signals and a circuit for processing analog signals, for example. The processor may include one or a plurality of circuit devices (e.g., an IC) or one or a plurality of circuit elements (e.g., a resistor, a capacitor) on a circuit board, for example. The processor may be a CPU (Central Processing Unit), for example, but this should not be construed in a limiting sense, and various types of processors including a GPU (Graphics Processing Unit) and a DSP (Digital Signal Processor) may be used. The processor may be a hardware circuit with an ASIC (Application Specific Integrated Circuit) or an FPGA (Field-Programmable Gate Array). The processor may include an amplification circuit, a filter circuit, or the like for processing analog signals. The memory may be a semiconductor memory such as an SRAM and a DRAM; a register; a magnetic storage device such as a hard disk device; and an optical storage device such as an optical disk device. The memory stores computer-readable instructions, for example. When the instructions are executed by the processor, the functions of each unit of the image processing device and the like are implemented. The instructions may be a set of instructions constituting a program or an instruction for causing an operation on the hardware circuit of the processor.

The units in the image processing apparatus and the like and the display device according to the present embodiment may be connected with each other via any types of digital data communication such as a communication network or via communication media. The communication network may include a LAN (Local Area Network), a WAN (Wide Area Network), and computers and networks which form the internet, for example.

What is claimed is:

1. An image processing apparatus, comprising:
   a processor comprising hardware, the processor being configured to:
   sequentially acquire plural subject images;

select a detection target image from the plural subject images;
detect a location of interest in the detection target image;
generate spatial information of a superimposed object, the superimposed object being to be superimposed on any one of the plural subject images and to indicate the location of interest;
select a superimposition target image from the plural subject images, the superimposition target image being a target on which the superimposed object is to be superimposed;
generate inter-image correspondence information between the detection target image and the superimposition target image;
correct the spatial information of the superimposed object, based on the inter-image correspondence information; and
superimpose the superimposed object on the superimposition target image, the superimposed object having the corrected spatial information,
wherein
the processor is further configured to repeatedly execute the selecting the superimposition target image, the generating the inter-image correspondence information, the correcting the spatial information, and the superimposing the superimposed object, until the spatial information of the superimposed object is generated for the detection target image.

2. The image processing apparatus according to claim 1, wherein the processor is further configured to execute a first process and a second process in parallel, the first process including the generating the spatial information of the superimposed object for the detection target image, and the second process including the selecting the superimposition target image, the generating the inter-image correspondence information, the correcting the spatial information, and the superimposing the superimposed object.

3. The image processing apparatus according to claim 2, further comprising a storage device that stores therein the spatial information of the superimposed object, wherein
the processor is further configured to:
compare an acquisition time of the detection target image defined as a first detection target image, from which the spatial information of the superimposed object is generated, the acquisition time being a time at which the subject image is acquired, with an acquisition time of the detection target image defined as a second detection target image, from which the latest spatial information of the superimposed object that has been generated and stored in the storage device; and
determine whether or not the spatial information of the superimposed object for the first detection target image is to be stored in the storage device.

4. The image processing apparatus according to claim 2, further comprising:
a storage device that stores therein the spatial information of the superimposed object, wherein
the processor is further configured to end the generating the spatial information, if an acquisition time of the detection target image, from which the spatial information of the superimposed object is generated, the acquisition time being a time at which the subject image is acquired, is earlier than an acquisition time of the detection target image, from which the latest spatial information of the superimposed object that has been generated and stored in the storage device.

5. The image processing apparatus according to claim 2, further comprising a storage device, wherein
the processor is further configured to:
generate the spatial information of the superimposed object for different detection target images in parallel;
store a plurality of the detection target images and plural pieces of spatial information of the superimposed object corresponding to the detection target images, in the storage device;
refer to the storage device; and
select the detection target image having been acquired at the latest acquisition time, as the detection target image to be used to generate the inter-image correspondence information.

6. The image processing apparatus according to claim 1, wherein the processor is further configured to time-divisionally execute the generating the spatial information of the superimposed object for the detection target image, in a time period, in which the selecting the superimposition target image, the generating the inter-image correspondence information, the correcting the spatial information, and the superimposing the superimposed object are repeatedly executed.

7. The image processing apparatus according to claim 1, wherein the processor is further configured to:
generate
inter-whole-image correspondence information between the detection target image and the superimposition target image, the inter-whole-image correspondence information being based on a whole area of the detection target image, and
inter-partial-image correspondence information between the detection target image and the superimposition target image, the inter-partial-image correspondence information being based on an area corresponding to a placement area of the superimposed object in the detection target image;
calculate
a first similarity between a first object area corresponding to the superimposed object in the detection target image, and a second object area in the superimposition target image, the second object area being associated with the first object area by use of the inter-whole-image correspondence information, and
a second similarity between the first object area and a third object area in the superimposition target image, the third object area being associated with the first object area by use of the inter-partial-image correspondence information; and
select one of the inter-whole-image correspondence information and the inter-partial-image correspondence information, as the inter-image correspondence information, based on the first similarity and the second similarity.

8. The image processing apparatus according to claim 1, further comprising a storage device, wherein
the processor is further configured to:
generate inter-image correspondence information between the new subject image acquired this time and another subject image acquired last time, when the subject image is newly acquired;
store the inter-image correspondence information sequentially in the storage device; and
generate the inter-image correspondence information by referring to the storage device and accumulating plural pieces of the inter-image correspondence information generated from when the subject image serving as the detection target image is acquired to when the subject image serving as the superimposition target image is acquired.

9. The image processing apparatus according to claim 1, wherein the processor is further configured to generate the inter-image correspondence information between the detection target image and the superimposition target image, by using a whole area of the detection target image.

10. The image processing apparatus according to claim 1, wherein the processor is further configured to generate the inter-image correspondence information between the detection target image and the superimposition target image, by using an area corresponding to a placement area of the superimposed object in the detection target image.

11. The image processing apparatus according to claim 1, wherein the processor is further configured to update the inter-image correspondence information, by comparing pixel values of corresponding areas between the detection target image and the superimposition target image, for the generated inter-image correspondence information.

12. The image processing apparatus according to claim 1, wherein the processor is further configured to generate information expressed by at least one coordinate transformation, as the inter-image correspondence information, the at least one coordinate transformation being selected from a group consisting of non-rigid transformation, homography transformation, affine transformation, linear transformation, scale transformation, rotational transformation, and translation.

13. The image processing apparatus according to claim 1, wherein the spatial information is at least one of a group consisting of representative coordinates, an area mask, and a contour line.

14. The image processing apparatus according to claim 1, wherein the processor is further configured to generate the spatial information of the superimposed object, based on detected information from a sensor.

15. An image processing method, comprising:
sequentially acquiring plural subject images;
selecting a detection target image from the plural subject images;
detecting a location of interest in the detection target image;
generating spatial information of a superimposed object, the superimposed object being to be superimposed on any of the plural subject images and to indicate the location of interest;
selecting a superimposition target image from the plural subject images, the superimposition target image being a target on which the superimposed object is to be superimposed;
generating inter-image correspondence information between the detection target image and the superimposition target image;
correcting the spatial information of the superimposed object, based on the inter-image correspondence information; and
superimposing the superimposed object on the superimposition target image, the superimposition target image having the corrected spatial information,
wherein
the selecting the superimposition target image, the generating the inter-image correspondence information, the correcting the spatial information, and the superimposing the superimposed object are repeatedly executed, until the spatial information of the superimposed object is generated for the detection target image.

16. A non-transitory computer-readable storage medium storing an image processing program that causes a computer to execute a process, the process comprising:
sequentially acquiring plural subject images;
selecting a detection target image from the plural subject images;
detecting a location of interest in the detection target image;
generating spatial information of a superimposed object, the superimposed object being to be superimposed on any of the plural subject images and to indicate the location of interest;
selecting a superimposition target image from the plural subject images, the plural subject images being a target on which the superimposed object is to be superimposed;
generating inter-image correspondence information between the detection target image and the superimposition target image;
correcting the spatial information of the superimposed object, based on the inter-image correspondence information; and
superimposing the superimposed object on the superimposition target image, the superimposed object having the corrected spatial information,
wherein
the selecting the superimposition target image, the generating the inter-image correspondence information, the correcting the spatial information, and the superimposing the superimposed object are repeatedly executed, until the spatial information of the superimposed object is generated for the detection target image.

* * * * *